US010676755B2

(12) United States Patent
Lincoln et al.

(10) Patent No.: US 10,676,755 B2
(45) Date of Patent: Jun. 9, 2020

(54) MUTATED ACETOHYDROXYACID SYNTHASE GENES IN EUPHORBIACEAE AND PLANT MATERIAL COMPRISING SUCH GENES

(71) Applicants: CIBUS US LLC, San Diego, CA (US); CIBUS EUROPE B.V., AD Kapelle (NL)

(72) Inventors: Tracey A. Lincoln, San Diego, CA (US); Gregory F. W. Gocal, San Diego, CA (US)

(73) Assignees: CIBUS US LLC, San Diego, CA (US); CIBUS EUROPE B.V., AD Kapelle (NL)

( * ) Notice: Subject to any disclaimer, the term of this patent is extended or adjusted under 35 U.S.C. 154(b) by 0 days.

(21) Appl. No.: 15/542,650

(22) PCT Filed: Jan. 8, 2016

(86) PCT No.: PCT/US2016/012717
§ 371 (c)(1),
(2) Date: Jul. 10, 2017

(87) PCT Pub. No.: WO2016/130247
PCT Pub. Date: Aug. 18, 2016

(65) Prior Publication Data
US 2017/0369899 A1 Dec. 28, 2017

Related U.S. Application Data

(60) Provisional application No. 62/102,010, filed on Jan. 10, 2015, provisional application No. 62/102,009, filed on Jan. 10, 2015.

(51) Int. Cl.
*C12N 15/82* (2006.01)
*C12N 9/88* (2006.01)

(52) U.S. Cl.
CPC ........... *C12N 15/8278* (2013.01); *C12N 9/88* (2013.01); *C12Y 401/03* (2013.01)

(58) Field of Classification Search
None
See application file for complete search history.

(56) References Cited

U.S. PATENT DOCUMENTS

| 7,094,606 B2 * | 8/2006 | Arntzen | C07K 14/43595 435/470 |
| 7,195,901 B1 * | 3/2007 | McKeon | C12N 9/1029 435/193 |
| 2009/0205064 A1 | 8/2009 | Schopke et al. | |
| 2010/0115650 A1 * | 5/2010 | Yao | C12N 9/88 800/260 |
| 2013/0042366 A1 | 2/2013 | Mankin et al. | |
| 2014/0245499 A1 * | 8/2014 | Uriarte | A01H 5/10 800/300 |

FOREIGN PATENT DOCUMENTS

| WO | 2008124495 A2 | 10/2008 |
| WO | 2010036771 A2 | 4/2010 |

OTHER PUBLICATIONS

Gianessi, L. Crop Life International, Aug. 2013, Herbicide Adoption Could Greatly Increase Cassava Production in Africa (Year: 2013).*
Le et al, GM Crops, Published online Mar. 1, 2010, vol. 1, Issue 2, pp. 62-67 (Year: 2010).*
Duggleby and Pang, Journal of Biochemistry and Molecular Biology, Jan. 2000, vol. 33, pp. 1-36 (Year: 2000).*
GenBank Accession No. EEF51778, Feb. 12, 2009, acetolactate synthase, Ricinus communis (Year: 2009).*
Prado et al, Weed Science, 2004, vol. 52, pp. 487-491 (Year: 2004).*
International Search Report and Written Opinion issued in PCT/US2016/012717 dated May 27, 2016 (16 pages).
Lee et al., "Single nucleotide mutation in the barley acetohydroxy acid synthase (AHAS) gene confers resistance to imidazolinone herbicides", Proc Natl Acad Sci U S A. May 24, 2011;108(21):8909-13. doi: 10.1073/pnas.1105612108. Epub May 5, 2011.
Tardif et al., "A mutation in the herbicide target site acetohydroxyacid synthase produces morphological and structural alterations and reduces fitness in Amaranthus powellii", New Phytol. 2006;169(2):251-64.
Exam Report issued by the Colombian Patent Office (CPO) in Colombian patent application No. NC2017/0007985 dated Mar. 29, 2019—incl Engl lang transl (26 pages total).
Exam Report issued by the Colombian Patent Office (CPO) in Colombian patent application number NC2017/007985 dated Oct. 3, 2019—incl Engl lang transl (15 pages total).
Chang et al., Herbicide-resistant forms of Arabidopsis thaliana acetohydroxyacid synthase: characterization of the catalytic properties and sensitivity to inhibitors of four defined mutants. Biochem J. Aug. 1, 1998;333 (Pt 3):765-777.
Exam Report issued by the Colombian Patent Office (CPO) in Colombian patent application No. NC2019/0008989 dated Jan. 22, 2020—incl Engl lang transl (15 pages total).

* cited by examiner

*Primary Examiner* — Eileen B O Hara
(74) *Attorney, Agent, or Firm* — Acuity Law Group, PC; Michael A. Whittaker

(57) ABSTRACT

Provided are mutated acetohydroxyacid synthase (AHAS) nucleic acids and the proteins encoded by the mutated nucleic acids. Also provided are cassava plants, cells, and seeds comprising the mutated genes.

15 Claims, 13 Drawing Sheets

Specification includes a Sequence Listing.

Fig. 1

SEQ ID NO: 1

```
MAAASTSAAT TIPKPSSHIS SSSRSSIFIS RFTLPLSLNP QKAIPHRSLH 50
ISNSVSKPTT PAPSSSTTLT IPQASPPRFS PDEARKGADI LVEALERQGV 100
TDVFAYPGGA SMEIHQALTR SPIIRNVLPR HEQGGVFAAE GYARASGKPG 150
VCIATSGPGA TNLVSGLADA LLDSVPIVAI TGQVPRRMIG TDAFQETPIV 200
EVTRSITKHN YLVLDVDDIP RIVSEAFFLA TSGRPGPVLI DVPKDIQQQL 250
AVPNWNTPIK LPGYMSRLPK VPNESHLEQI VRLIFESKKP VLYVGGGCLN 300
SSEELRKFVE LTGIPVASTL MGLGAFPVGH ELSLQMLGMH GTVYANYSVD 350
KSDLLLAFGV RFDDRVTGKL EAFASRAKIV HIDIDSAEIG KNKQPHVSVC 400
ADVKFALQGM NKILESRCAK SKLDFKAWRE ELNEQKSKYP LKYKTFGDAI 450
PPQYAIQVLD ELTDGNAIIS TGVGQHQMWA AQFYKYKRPR QWLTSGGLGA 500
MGFGLPAAIG AAVANPGAVV VDIDGDGSFI MNVQELATIR VENLPIKIML 550
LNNQHLGMVV QWEDRFYKAN RAHTYLGDPS KESEIFPNML KFAEACGIPA 600
ARVTRKEGLR MAIQKMLDTP GPYLLDVIVP HQEHVLPMIP SGGAFKDVIT 650
EGDGRTKY
```

Fig. 2

SEQ ID NO: 2

ATGGCGGCGGCGTCTACCTCTGCGGCTACCACTATCCCTAAACCCTCTTCTCACATTTCT
TCCTCCTCCAGATCTTCAATCTTCATTTCCAGATTCACCCTCCCATTGTCTCTCAACCCC
CAAAAGGCCATTCCTCACCGCTCTCTCCACATATCAAACTCTGTCTCTAAACCTACAACC
CCTGCCCCCTCATCCTCCACCACCTTAACCATTCCTCAAGCGTCTCCTCCCAGGTTTTCT
CCTGATGAAGCTCGAAAAGGCGCCGACATCCTCGTTGAAGCGCTGGAACGCCAAGGGGTC
ACTGATGTATTTGCTTATCCAGGCGGCGCATCCATGGAGATCCATCAAGCCCTGACTCGC
TCACCTATAATTCGCAATGTCCTCCCGCGCCATGAGCAAGGTGGGGTCTTTGCGGCTGAG
GGATATGCTCGCGCTTCTGGCAAGCCTGGCGTCTGTATCGCAACCTCGGGACCCGGCGCT
ACAAATCTCGTAAGTGGCTTGGCAGACGCTCTCCTTGACAGCGTCCCCATTGTGGCTATC
ACCGGCCAAGTTCCTCGCCGCATGATTGGCACCGACGCATTCCAAGAAACTCCCATTGTT
GAGGTAACTCGGTCAATAACTAAGCACAATTACCTGGTCCTTGATGTTGATGATATTCCT
AGAATTGTAAGTGAAGCTTTCTTTTTGGCCACCTCGGGACGTCCTGGCCCAGTTCTGATT
GATGTACCAAAAGATATACAACAACAATTAGCTGTTCCAAATTGGAATACACCTATTAAA
TTGCCTGGTTACATGTCGAGGTTGCCTAAAGTGCCCAACGAATCACATTTGGAGCAGATT
GTGAGGCTAATTTTTGAGTCAAAGAAACCGGTTTTATACGTGGGAGGTGGGTGTTTAAAT
TCAAGTGAGGAGTTGAGAAAGTTTGTCGAGTTAACTGGGATCCCAGTGGCTAGTACTTTG
ATGGGGCTCGGAGCATTCCCAGTTGGCCACGAATTGTCATTACAAATGCTTGGAATGCAT
GGAACTGTTTATGCTAACTACTCGGTGGATAAGAGTGATTTGTTGCTTGCGTTTGGGGTG
AGGTTTGATGACAGGGTGACAGGCAAGCTTGAGGCCTTTGCAAGCAGAGCTAAGATTGTT
CACATTGATATTGATTCCGCTGAGATTGGGAAAAATAAGCAGCCCCATGTGTCTGTTTGT
GCAGATGTGAAGTTTGCCTTGCAAGGGATGAACAAGATTTTGGAGAGCAGATGTGCTAAG
AGTAAGCTAGATTTAAGGCTTGGAGGGAGGAGTTGAATGAGCAGAAAGTAAATATCCA
TTGAAATACAAGACATTTGGAGATGCAATTCCTCCTCAGTACGCCATACAAGTTCTCGAT
GAATTAACAGATGGGAATGCCATTATAAGTACTGGCGTTGGACAACATCAGATGTGGGCT
GCTCAATTTACAAGTACAAGAGACCACGGCAATGGTTGACGTCAGGGGGATTAGGGGCT
ATGGGTTTTGGATTGCCTGCCGCCATTGGGGCTGCTGTTGCTAATCCTGGTGCAGTTGTT
GTAGATATTGATGGTGATGGAAGTTTTATCATGAATGTCCAGGAGTTGGCAACAATTCGT
GTGGAGAATCTGCCAATTAAAATAATGCTTTTGAATAATCAGCATTTGGGAATGGTGGTA
CAATGGGAGGACCGATTCTACAAGGCTAATAGAGCTCATACTTATTTGGGGGATCCATCA

Fig. 2 continued

```
AAGGAGTCTGAGATTTTCCCCAATATGTTGAAGTTTGCAGAAGCTTGTGGAATACCTGCT
GCTCGCGTGACAAGAAAAGAGGGTCTTAGAATGGCGATTCAGAAAATGCTAGATACTCCA
GGGCCATACTTGTTGGATGTGATTGTGCCCCATCAAGAACATGTGCTGCCCATGATCCCA
AGTGGGGGAGCTTTTAAGGATGTGATAACTGAGGGTGATGGAAGAACGAAGTATTGA
```

Fig. 3A

SEQ ID NO: 5

MAAASTSAAT TIPKPSSHIS SSSRSSIFIS RFTLPLSLNP QKAIPHRSLH
ISNSVSKPTT PAPSSTTLT IPQASPPRFS PDEARKGADI LVEALERQGV
TDVFAYPGGA SMEIHQALTR SPIIRNVLPR HEQGGVFAAE GYARASGKPG
VCIATSGPGA TNLVSGLADA LLDSVPIVAI TGQVPRRMIG TDAFQETPIV
EVTRSITKHN YLVLDVDDIP RIVSEAFFLA TSGRPGPVLI DVPKDIQQQL
AVPNWNTPIK LPGYMSRLPK VPNESHLEQI VRLIFESKKP VLYVGGGCLN
SSEELRKFVE LTGIPVASTL MGLGAFPVGH ELSLQMLGMH GTVYANYSVD
KSDLLLAFGV RFD<u>A</u>RVTGKL EAFASRAKIV HIDIDSAEIG KNKQPHVSVC
ADVKFALQGM NKILESRCAK SKLDFKAWRE ELNEQKSKYP LKYKTFGDAI
PPQYAIQVLD ELTDGNAIIS TGVGQHQMWA AQFYKYKRPR QWLTSGGLGA
MGFGLPAAIG AAVANPGAVV VDIDGDGSFI MNVQELATIR VENLPIKIML
LNNQHLGMVV QSEDRFYKAN RAHTYLGDPS KESEIFPNML KFAEACGIPA
ARVTRKEGLR MAIQKMLDTP GPYLLDVIVP HQEHVLPMIP SGGAFKDVIT
EGDGRTKY

Fig. 3B

SEQ ID NO: 3

```
MAAASTSAAT TIPKPSSHIS SSSRSSIFIS RFTLPLSLNP QKAIPHRSLH
ISNSVSKPTT PAPSSSTTLT IPQASPPRFS PDEARKGADI LVEALERQGV
TDVFAYPGGA SMEIHQALTR SPIIRNVLPR HEQGGVFAAE GYARASGKPG
VCIATSGPGA TNLVSGLADA LLDSVPIVAI TGQVPRRMIG TDAFQETPIV
EVTRSITKHN YLVLDVDDIP RIVSEAFFLA TSGRPGPVLI DVPKDIQQQL
AVPNWNTPIK LPGYMSRLPK VPNESHLEQI VRLIFESKKP VLYVGGGCLN
SSEELRKFVE LTGIPVASTL MGLGAFPVGH ELSLQMLGMH GTVYANYSVD
KSDLLLAFGV RFDDRVTGKL EAFASRAKIV HIDIDSAEIG KNKQPHVSVC
ADVKFALQGM NKILESRCAK SKLDFKAWRE ELNEQKSKYP LKYKTFGDAI
PPQYAIQVLD ELTDGNAIIS TGVGQHQMWA AQFYKYKRPR QWLTSGGLGA
MGFGLPAAIG AAVANPGAVV VDIDGDGSFI MNVQELATIR VENLPIKIML
LNNQHLGMVV QSEDRFYKAN RAHTYLGDPS KESEIFPNML KFAEACGIPA
ARVTRKEGLR MAIQKMLDTP GPYLLDVIVP HQEHVLPMIP SGGAFKDVIT
EGDGRTKY
```

Fig. 4

```
SEQ ID NO: 4

Met Ala Ala Ala Thr Thr Thr Thr Thr Thr Ser Ser Ser Ile Ser Phe
Ser Thr Lys Pro Ser Pro Ser Ser Ser Lys Ser Pro Leu Pro Ile Ser
Arg Phe Ser Leu Pro Phe Ser Leu Asn Pro Asn Lys Ser Ser Ser Ser
Ser Arg Arg Arg Gly Ile Lys Ser Ser Ser Pro Ser Ser Ile Ser Ala
Val Leu Asn Thr Thr Thr Asn Val Thr Thr Thr Pro Ser Pro Thr Lys
Pro Thr Lys Pro Glu Thr Phe Ile Ser Arg Phe Ala Pro Asp Gln Pro
Arg Lys Gly Ala Asp Ile Leu Val Glu Ala Leu Glu Arg Gln Gly Val
Glu Thr Val Phe Ala Tyr Pro Gly Gly Ala Ser Met Glu Ile His Gln
Ala Leu Thr Arg Ser Ser Ser Ile Arg Asn Val Leu Pro Arg His Glu
Gln Gly Gly Val Phe Ala Ala Glu Gly Tyr Ala Arg Ser Ser Gly Lys
Pro Gly Ile Cys Ile Ala Thr Ser Gly Pro Gly Ala Thr Asn Leu Val
Ser Gly Leu Ala Asp Ala Leu Leu Asp Ser Val Pro Leu Val Ala Ile
Thr Gly Gln Val Pro Arg Arg Met Ile Gly Thr Asp Ala Phe Gln Glu
Thr Pro Ile Val Glu Val Thr Arg Ser Ile Thr Lys His Asn Tyr Leu
Val Met Asp Val Glu Asp Ile Pro Arg Ile Ile Glu Glu Ala Phe Phe
Leu Ala Thr Ser Gly Arg Pro Gly Pro Val Leu Val Asp Val Pro Lys
Asp Ile Gln Gln Gln Leu Ala Ile Pro Asn Trp Glu Gln Ala Met Arg
Leu Pro Gly Tyr Met Ser Arg Met Pro Lys Pro Pro Glu Asp Ser His
Leu Glu Gln Ile Val Arg Leu Ile Ser Glu Ser Lys Lys Pro Val Leu
Tyr Val Gly Gly Gly Cys Leu Asn Ser Ser Asp Glu Leu Gly Arg Phe
Val Glu Leu Thr Gly Ile Pro Val Ala Ser Thr Leu Met Gly Leu Gly
Ser Tyr Pro Cys Asp Asp Glu Leu Ser Leu His Met Leu Gly Met His
Gly Thr Val Tyr Ala Asn Tyr Ala Val Glu His Ser Asp Leu Leu Leu
Ala Phe Gly Val Arg Phe Asp *Asp* Arg Val Thr Gly Lys Leu Glu Ala
```

Fig. 4 Continued

Phe Ala Ser Arg Ala Lys Ile Val His Ile Asp Ile Asp Ser Ala Glu

Ile Gly Lys Asn Lys Thr Pro His Val Ser Val Cys Gly Asp Val Lys

Leu Ala Leu Gln Gly Met Asn Lys Val Leu Glu Asn Arg Ala Glu Glu

Leu Lys Leu Asp Phe Gly Val Trp Arg Asn Glu Leu Asn Val Gln Lys

Gln Lys Phe Pro Leu Ser Phe Lys Thr Phe Gly Glu Ala Ile Pro Pro

Gln Tyr Ala Ile Lys Val Leu Asp Glu Leu Thr Asp Gly Lys Ala Ile

Ile Ser Thr Gly Val Gly Gln His Gln Met Trp Ala Ala Gln Phe Tyr

Asn Tyr Lys Lys Pro Arg Gln Trp Leu Ser Ser Gly Gly Leu Gly Ala

Met Gly Phe Gly Leu Pro Ala Ala Ile Gly Ala Ser Val Ala Asn Pro

Asp Ala Ile Val Val Asp Ile Asp Gly Asp Gly Ser Phe Ile Met Asn

Val Gln Glu Leu Ala Thr Ile Arg Val Glu Asn Leu Pro Val Lys Val

Leu Leu Leu Asn Asn Gln His Leu Gly Met Val Met Gln <u>Trp</u> Glu Asp

Arg Phe Tyr Lys Ala Asn Arg Ala His Thr Phe Leu Gly Asp Pro Ala

Gln Glu Asp Glu Ile Phe Pro Asn Met Leu Leu Phe Ala Ala Ala Cys

Gly Ile Pro Ala Ala Arg Val Thr Lys Lys Ala Asp Leu Arg Glu Ala

Ile Gln Thr Met Leu Asp Thr Pro Gly Pro Tyr Leu Leu Asp Val Ile

Cys Pro His Gln Glu His Val Leu Pro Met Ile Pro Ser Gly Gly Thr

Phe Asn Asp Val Ile Thr Glu Gly Asp Gly Arg Ile Lys Tyr

MUTATED ACETOHYDROXYACID SYNTHASE GENES IN EUPHORBIACEAE AND PLANT MATERIAL COMPRISING SUCH GENES

The present invention is filed under 35 U.S.C. § 371 as the U.S. national phase of International Patent Application No. PCT/US2016/012717, filed Jan. 8, 2016, which designated the United States and claims the benefit of U.S. Provisional Application No. 62/102,009, filed Jan. 10, 2015, and U.S. Provisional Application No. 62/102,010, filed Jan. 10, 2015, each of which is hereby incorporated in its entirety and from which priority is claimed.

SEQUENCE LISTING

The instant application contains a Sequence Listing which has been submitted in ASCII format via EFS-Web and is hereby incorporated by reference in its entirety. Said ASCII copy, created on Jul. 10, 2017, is named CIBUS_03.2_US_SeqListing.txt and is 27 kilobytes in size

FIELD OF THE INVENTION

This invention relates to the field of herbicide resistant plants and seeds and more specifically to mutations in the acetohydroxyacid synthase (AHAS) gene and protein.

BACKGROUND OF THE INVENTION

The following description is provided simply as an aid in understanding the invention and is not admitted to describe or constitute prior art to the invention.

Cassava (*Manihot esculenta*), castor bean (*Ricinus communis*), rubber tree (*Hevea brasiliensis*), Barbados nut (*Jatropha curcas*), ornamental poinsettias (*Euphorbia pulcherrima*), and the invasive weed leafy spurge (*Euphorbia esula*) are among the economically important members of the Euphorbiaceae family. A more complete list of genera within the family is as follows:

Genus *Acalypha* L. - copperleaf
Genus *Adelia* L. - wild lime
Genus *Alchornea* Sw. - alchornea
Genus *Alchorneopsis* Mull. Arg. - alchorneopsis
Genus *Aleurites* J. R. Forst. & G. Forst. - aleurites
Genus *Antidesma* L. - chinalaurel
Genus *Argythamnia* P. Br. - silverbush
Genus *Baccaurea* Lour. - baccaurea
Genus *Bernardia* Mill. - myrtlecroton
Genus *Bischofia* Blume - bishopwood
Genus *Breynia* J. R. Forst. & G. Forst. - breynia
Genus *Caperonia* A. St.-Hil. - false croton
Genus *Chamaesyce* Gray - sandmat
Genus *Chrozophora* A. Juss. - chrozophora
Genus *Claoxylon* A. Juss. - claoxylon
Genus *Cnidoscolus* Pohl - cnidoscolus
Genus *Codiaeum* Juss. - codiaeum
Genus *Croton* L. - croton
Genus *Dalechampia* L. - dalechampia
Genus *Ditrysinia* Raf. - Sebastian-bush
Genus *Ditta* Griseb. - ditta
Genus *Drypetes* Vahl - drypetes
Genus *Euphorbia* L. - spurge
Genus *Excoecaria* L.
Genus *Flueggea* Willd. - bushweed
Genus *Garcia* Rohr
Genus *Glochidion* J. R. Forst. & G. Forst. - glochidion
Genus *Gymnanthes* Sw. - gymnanthes
Genus *Hevea* Aubl. - hevea
Genus *Hippomane* L. - hippomane
Genus *Hura* L. - sandbox tree
Genus *Hyeronima* Allemao - hyeronima
Genus *Jatropha* L. - nettlespurge
Genus *Leptopus* Decne. - maidenbush
Genus *Macaranga* Thouars - macaranga
Genus *Mallotus* Lour. - mallotus
Genus *Manihot* Mill. - cassava
Genus *Margaritaria* L. f. - margaritaria
Genus *Melanolepis* Rchb. f. & Zoll.
Genus *Mercurialis* L. - mercurialis
Genus *Micrandra* Benth. - micrandra
Genus *Microstachys* Juss. - microstachys
Genus *Pedilanthus* Neck. ex Poit. - pedilanthus
Genus *Pera* Mutis - pera
Genus *Phyllanthus* L. - leafflower
Genus *Reutealis* Airy Shaw - reutealis
Genus *Reverchonia* A. Gray - reverchonia
Genus *Ricinodendron* Mull. Arg. - ricinodendron
Genus *Ricinus* L. - ricinus
Genus *Sapium* Jacq. - milktree
Genus *Sauropus* Blume - sauropus
Genus *Savia* Willd. - savia
Genus *Sebastiania* Spreng. - Sebastian-bush
Genus *Stillingia* Garden ex L. - toothleaf
Genus *Tetracarpidium* Pax - tetracarpidium
Genus *Tetracoccus* Engelm. ex Parry - shrubby-spurge
Genus *Tragia* L. - noseburn
Genus *Triadica* Loureiro - Chinese tallow
Genus *Vaupesia* R. E. Schult. - vaupesia
Genus *Vernicia* Lour. - vernicia Benefits of herbicide-tolerant plants are known. For example, herbicide-tolerant plants may reduce the need for tillage to control weeds thereby effectively reducing soil erosion.

SUMMARY OF THE INVENTION

The disclosure relates in part to mutated Euphorbiaceae acetohydroxyacid synthase (AHAS) nucleic acids and the proteins encoded by the mutated nucleic acids. The disclosure also relates in part to cassava plants, cells, and seeds comprising these mutated nucleic acids and proteins.

In one aspect, there is provided an isolated nucleic acid encoding a Euphorbiaceae acetohydroxyacid synthase protein having a mutation at one or more amino acid positions, one of which corresponds to a tryptophan to serine mutation at position 574 (referred to herein as a W574S mutation). The residue numbering, and thus the position of the mutation at tryptophan 574, is presented relative to the *Arabidopsis* residue numbering. In some embodiments, the Euphorbiaceae is Cassava (*Manihot esculenta*), castor bean (*Ricinus communis*), rubber tree (*Hevea brasiliensis*), Barbados nut (*Jatropha curcas*), or ornamental poinsettia (*Euphorbia pulcherrima*). In some embodiments, the isolated nucleic acid encodes a protein having one or more mutations, one of which corresponds to a tryptophan to serine mutation at position 562 of SEQ ID NO: 1, where SEQ ID NO: 1 represents a Cassava AHAS protein sequence. In some embodiments, the Euphorbiaceae acetohydroxyacid synthase (AHAS) protein comprising the W574S mutation is resistant to inhibition by an AHAS-inhibiting herbicide. In some embodiments, the AHAS-inhibiting herbicide is selected from the group consisting of herbicides of: imidazolinone, sulfonylurea, triazolopyrimidine, pyrimidinylthiobenzoate, sulfonylamino-carbonyltriazolinone, and mixtures thereof. In some embodiments, the herbicide is an imidazolinone herbicide. In some embodiments, the herbicide is a sulfonylurea herbicide.

In another aspect, there is provided an expression vector containing an isolated nucleic acid encoding a Euphorbiaceae acetohydroxyacid synthase protein having a mutation at one or more amino acid positions, one of which corresponds to a W574S mutation. In some embodiments, the Euphorbiaceae is Cassava (*Manihot esculenta*), rubber tree (*Hevea brasiliensis*), Barbados nut (*Jatropha curcas*), or ornamental poinsettia (*Euphorbia pulcherrima*). In some embodiments, the isolated nucleic acid encodes a protein having one or more mutations, one of which corresponds to a tryptophan to serine mutation at position 562 of SEQ ID NO: 1, where SEQ ID NO: 1 represents a Cassava AHAS protein sequence. In some embodiments, isolated nucleic acid encodes a protein that is resistant to the application of at least one AHAS-inhibiting herbicide. In some embodiments, the AHAS-inhibiting herbicide is selected from the group consisting of herbicides of: imidazolinone, sulfonylurea, triazolopyrimidine, pyrimidinylthiobenzoate, sulfonylamino-carbonyltriazolinone, and mixtures thereof. In some embodiments, the herbicide is an imidazolinone herbicide. In some embodiments, the herbicide is a sulfonylurea herbicide.

In another aspect, there is provided a plant having a Euphorbiaceae acetohydroxyacid synthase gene, in which the gene encodes a protein having a mutation at one or more amino acid positions, one of which corresponds to a W574S mutation. In another aspect, there is provided a plant having a Euphorbiaceae acetohydroxyacid synthase gene, in which the plant is resistant to an AHAS-inhibiting herbicide, in which the gene encodes a protein having a mutation at one or more amino acid positions, one of which corresponds to a W574S mutation. In some embodiments, the Euphorbiaceae is Cassava (*Manihot esculenta*), castor bean (*Ricinus communis*), rubber tree (*Hevea brasiliensis*), Barbados nut (*Jatropha curcas*), or ornamental poinsettia (*Euphorbia pulcherrima*). In some embodiments, the isolated nucleic acid encodes a protein having one or more mutations, one of which corresponds to a tryptophan to serine mutation at position 562 of SEQ ID NO: 1, where SEQ ID NO: 1 represents a Cassava AHAS protein sequence. In some embodiments, the plant is resistant to the application of at least one AHAS-inhibiting herbicide. In some embodiments, the AHAS-inhibiting herbicide is selected from the group consisting of herbicides of: imidazolinone, sulfonylurea, triazolopyrimidine, pyrimidinylthiobenzoate, sulfonylamino-carbonyltriazolinone, and mixtures thereof. In some embodiments, the herbicide is an imidazolinone herbicide. In some embodiments, the herbicide is a sulfonylurea herbicide. In some embodiments, the plant is a Cassava (*Manihot esculenta*), castor bean (*Ricinus communis*), rubber tree (*Hevea brasiliensis*), Barbados nut (*Jatropha curcas*), or ornamental poinsettia (*Euphorbia pulcherrima*). In some embodiments, the plant is non-transgenic.

In one aspect there is provided a seed having a Euphorbiaceae acetohydroxyacid synthase gene, in which the gene encodes a protein having a mutation at one or more amino acid positions, one of which corresponds to a W574S mutation. In another aspect, there is provided a seed having a Euphorbiaceae acetohydroxyacid synthase gene, in which the seed is from a Euphorbiaceae plant that is resistant to an AHAS-inhibiting herbicide, in which the gene encodes a protein having a mutation at one or more amino acid positions, one of which corresponds to a W574S mutation. In some embodiments, the Euphorbiaceae is Cassava (*Manihot esculenta*), castor bean (*Ricinus communis*), rubber tree (*Hevea brasiliensis*), Barbados nut (*Jatropha curcas*), or ornamental poinsettia (*Euphorbia pulcherrima*). In some embodiments, the gene encodes a protein having one or more mutations, one of which corresponds to a tryptophan to serine mutation at position 562 of SEQ ID NO: 1, where SEQ ID NO: 1 represents a Cassava AHAS protein sequence. In some embodiments, the seed is from a Euphorbiaceae plant that is resistant to the application of at least one AHAS-inhibiting herbicide. In some embodiments, the AHAS-inhibiting herbicide is selected from the group consisting of herbicides of: imidazolinone, sulfonylurea, triazolopyrimidine, pyrimidinylthiobenzoate, sulfonylamino-carbonyltriazolinone, and mixtures thereof. In some embodiments, the herbicide is an imidazolinone herbicide. In some embodiments, the herbicide is a sulfonylurea herbicide. In some embodiments, the seed is from a Cassava (*Manihot esculenta*), castor bean (*Ricinus communis*), rubber tree (*Hevea brasiliensis*), Barbados nut (*Jatropha curcas*), or ornamental poinsettia (*Euphorbia pulcherrima*). In some embodiments, the seed is from a Euphorbiaceae plant that is non-transgenic.

In another aspect, there is provided a method for producing an herbicide-resistant Euphorbiaceae plant by introducing into a Euphorbiaceae plant cell a gene repair oligonucleobase (GRON) with a targeted mutation in an acetohydroxyacid synthase (AHAS) gene to produce a plant cell with an AHAS gene that expresses an AHAS protein having a mutation at one or more amino acid positions, one of which corresponds to a W574S mutation; and identifying a Euphorbiaceae plant cell modified thereby but having substantially normal growth and catalytic activity as compared to a corresponding wild-type plant cell in the presence of an AHAS-inhibiting herbicide; and regenerating a non-transgenic herbicide-resistant Euphorbiaceae plant having a mutated AHAS gene from said plant cell. In another aspect, there is provided a method for increasing the herbicide-resistance of a plant by: (a) crossing a first Euphorbiaceae plant to a second Euphorbiaceae plant, in which the first plant comprises a Euphorbiaceae acetohydroxyacid synthase gene, in which the gene encodes a protein having a mutation at one or more amino acid positions, one of which corresponds to a W574S mutation; (b) screening a population resulting from the cross for increased AHAS herbicide-resistance; (c) selecting a member resulting from the cross having increased AHAS herbicide-resistance; and (d) producing seeds resulting from the cross. In some embodiments, a hybrid seed is produced by any of the above methods. In some embodiments, plants are grown from seeds produced by any of the above methods. In another aspect, there is provided a method of controlling weeds in a field containing plants by applying an effective amount of at least one AHAS-inhibiting herbicide to a field containing said weeds and plants, the plant having a Euphorbiaceae acetohydroxyacid synthase (AHAS) gene, in which the gene encodes a protein having a mutation at one or more amino acid positions, one of which corresponds to a W574S mutation. In some embodiments, the AHAS-inhibiting herbicide is selected from the group consisting of herbicides of: imidazolinone, sulfonylurea, triazolopyrimidine, pyrimidinylthiobenzoate, sulfonylamino-carbonyltriazolinone, and mixtures thereof. In other embodiments, the AHAS-inhibiting herbicide is an imidazolinone herbicide. In other embodiments, the AHAS-inhibiting herbicide is a sulfonylurea herbicide.

In the aspects described herein the W574S mutation may be combined with one or more additional mutations in the protein sequence. By way of example, such mutations may include one or more of a serine to threonine substitution at a position corresponding to position 653, a serine to asparagine substitution at a position corresponding to position 653, an alanine to valine substitution at a position corresponding to position 205, an alanine to aspartic acid substitution at a position corresponding to position 205, an aspartic acid to glutamic acid substitution at a position corresponding to position 376, an arginine to tryptophan substitution at a position corresponding to position 577, in each case the position numbering is recited relative to the *Arabidopsis* residue numbering.

In another aspect, there is provided an isolated nucleic acid encoding a Euphorbiaceae acetohydroxyacid synthase protein having a mutation at one or more amino acid positions, one of which corresponds to an aspartic acid to alanine mutation at position 376 (referred to herein as a D376A mutation). The residue numbering, and thus the position of the mutation at aspartic acid 376, is presented relative to the *Arabidopsis* residue numbering. In some embodiments, the Euphorbiaceae is Cassava (*Manihot esculenta*), castor bean (*Ricinus communis*), rubber tree (*Hevea brasiliensis*), Barbados nut (*Jatropha curcas*), or ornamental poinsettia (*Euphorbia pulcherrima*). In some embodiments, the isolated nucleic acid encodes a protein having one or more mutations, one of which corresponds to an aspartic acid to alanine mutation at position 364 of SEQ ID NO: 1, where SEQ ID NO: 1 represents a Cassava AHAS protein sequence. In some embodiments, the Euphorbiaceae acetohydroxyacid synthase (AHAS) protein comprising the D376A mutation is resistant to inhibition by an AHAS-inhibiting herbicide. In some embodiments, the AHAS-inhibiting herbicide is selected from the group consisting of herbicides of: imidazolinone, sulfonylurea, triazolopyrimidine, pyrimidinylthiobenzoate, sulfonylamino-carbonyltriazolinone, and mixtures thereof. In some embodiments, the herbicide is an imidazolinone herbicide. In some embodiments, the herbicide is a sulfonylurea herbicide.

In another aspect, there is provided an expression vector containing an isolated nucleic acid encoding a Euphorbiaceae acetohydroxyacid synthase protein having a mutation at one or more amino acid positions, one of which corresponds to a D376A mutation. In some embodiments, the Euphorbiaceae is Cassava (*Manihot esculenta*), rubber tree (*Hevea brasiliensis*), Barbados nut (*Jatropha curcas*), or ornamental poinsettia (*Euphorbia pulcherrima*). In some embodiments, the isolated nucleic acid encodes a protein having one or more mutations, one of which corresponds to an aspartic acid to alanine mutation at position 364 of SEQ ID NO: 1, where SEQ ID NO: 1 represents a Cassava AHAS protein sequence. In some embodiments, isolated nucleic acid encodes a protein that is resistant to the application of at least one AHAS-inhibiting herbicide. In some embodiments, the AHAS-inhibiting herbicide is selected from the group consisting of herbicides of: imidazolinone, sulfonylurea, triazolopyrimidine, pyrimidinylthiobenzoate, sulfonylamino-carbonyltriazolinone, and mixtures thereof. In some embodiments, the herbicide is an imidazolinone herbicide. In some embodiments, the herbicide is a sulfonylurea herbicide.

In another aspect, there is provided a plant having a Euphorbiaceae acetohydroxyacid synthase gene, in which the gene encodes a protein having a mutation at one or more amino acid positions, one of which corresponds to a D376A mutation. In another aspect, there is provided a plant having a Euphorbiaceae acetohydroxyacid synthase gene, in which the plant is resistant to an AHAS-inhibiting herbicide, in which the gene encodes a protein having a mutation at one or more amino acid positions, one of which corresponds to a D376A mutation. In some embodiments, the Euphorbiaceae is Cassava (*Manihot esculenta*), castor bean (*Ricinus communis*), rubber tree (*Hevea brasiliensis*), Barbados nut (*Jatropha curcas*), or ornamental poinsettia (*Euphorbia pulcherrima*). In some embodiments, the isolated nucleic acid encodes a protein having one or more mutations, one of which corresponds to an aspartic acid to alanine mutation at position 364 of SEQ ID NO: 1, where SEQ ID NO: 1 represents a Cassava AHAS protein sequence. In some embodiments, the plant is resistant to the application of at least one AHAS-inhibiting herbicide. In some embodiments, the AHAS-inhibiting herbicide is selected from the group consisting of herbicides of: imidazolinone, sulfonylurea, triazolopyrimidine, pyrimidinylthiobenzoate, sulfonylamino-carbonyltriazolinone, and mixtures thereof. In some embodiments, the herbicide is an imidazolinone herbicide. In some embodiments, the herbicide is a sulfonylurea herbicide. In some embodiments, the plant is a Cassava (*Manihot esculenta*), castor bean (*Ricinus communis*), rubber tree (*Hevea brasiliensis*), Barbados nut (*Jatropha curcas*), or ornamental poinsettia (*Euphorbia pulcherrima*). In some embodiments, the plant is non-transgenic.

In one aspect there is provided a seed having a Euphorbiaceae acetohydroxyacid synthase gene, in which the gene encodes a protein having a mutation at one or more amino acid positions, one of which corresponds to a D376A mutation. In another aspect, there is provided a seed having a Euphorbiaceae acetohydroxyacid synthase gene, in which the seed is from a Euphorbiaceae plant that is resistant to an AHAS-inhibiting herbicide, in which the gene encodes a protein having a mutation at one or more amino acid positions, one of which corresponds to a D376A mutation. In some embodiments, the Euphorbiaceae is Cassava (*Manihot esculenta*), castor bean (*Ricinus communis*), rubber tree (*Hevea brasiliensis*), Barbados nut (*Jatropha curcas*), or ornamental poinsettia (*Euphorbia pulcherrima*). In some embodiments, the gene encodes a protein having one or more mutations, one of which corresponds to an aspartic acid to alanine mutation at position 364 of SEQ ID NO: 1, where SEQ ID NO: 1 represents a Cassava AHAS protein sequence. In some embodiments, the seed is from a Euphorbiaceae plant that is resistant to the application of at least one AHAS-inhibiting herbicide. In some embodiments, the AHAS-inhibiting herbicide is selected from the group consisting of herbicides of: imidazolinone, sulfonylurea, triazolopyrimidine, pyrimidinylthiobenzoate, sulfonylamino-carbonyltriazolinone, and mixtures thereof. In some embodiments, the herbicide is an imidazolinone herbicide. In some embodiments, the herbicide is a sulfonylurea herbicide. In some embodiments, the seed is from a Cassava (*Manihot esculenta*), castor bean (*Ricinus communis*), rubber tree (*Hevea brasiliensis*), Barbados nut (*Jatropha curcas*), or ornamental poinsettia (*Euphorbia pulcherrima*). In some embodiments, the seed is from a Euphorbiaceae plant that is non-transgenic.

In another aspect, there is provided a method for producing an herbicide-resistant Euphorbiaceae plant by introducing into a Euphorbiaceae plant cell a gene repair oligonucleobase (GRON) with a targeted mutation in an acetohydroxyacid synthase (AHAS) gene to produce a plant cell with an AHAS gene that expresses an AHAS protein having a mutation at one or more amino acid positions, one of which corresponds to a D376A mutation; and identifying a Euphorbiaceae plant cell modified thereby but having substantially normal growth and catalytic activity as compared to a corresponding wild-type plant cell in the presence of an AHAS-inhibiting herbicide; and regenerating a non-transgenic herbicide-resistant Euphorbiaceae plant having a mutated AHAS gene from said plant cell. In another aspect, there is provided a method for increasing the herbicide-resistance of a plant by: (a) crossing a first Euphorbiaceae plant to a second Euphorbiaceae plant, in which the first plant comprises a Euphorbiaceae acetohydroxyacid synthase gene, in which the gene encodes a protein having a mutation at one or more amino acid positions, one of which corresponds to a D376A mutation; (b) screening a population resulting from the cross for increased AHAS herbicide-resistance; (c) selecting a member resulting from the cross having increased AHAS herbicide-resistance; and (d) producing seeds resulting from the cross. In some embodiments, a hybrid seed is produced by any of the above methods. In some embodiments, plants are grown from seeds produced by any of the above methods. In another aspect, there is provided a method of controlling weeds in a field containing plants by applying an effective amount of at least one AHAS-inhibiting herbicide to a field containing said weeds and plants, the plant having a Euphorbiaceae acetohydroxyacid synthase (AHAS) gene, in which the gene encodes a protein having a mutation at one or more amino acid positions, one of which corresponds to a D376A mutation. In some embodiments, the AHAS-inhibiting herbicide is selected from the group consisting of herbicides of: imidazolinone, sulfonylurea, triazolopyrimidine, pyrimidinylthiobenzoate, sulfonylamino-carbonyltriazolinone, and mixtures thereof. In other embodiments, the AHAS-inhibiting herbicide is an imidazolinone herbicide. In other embodiments, the AHAS-inhibiting herbicide is a sulfonylurea herbicide.

In the aspects described herein the D376A mutation may be combined with one or more additional mutations in the protein sequence. By way of example, such mutations may include one or more of a serine to threonine substitution at a position corresponding to position 653, a serine to asparagine substitution at a position corresponding to position 653, an alanine to valine substitution at a position corresponding to position 205, an alanine to aspartic acid substitution at a position corresponding to position 205, an arginine to tryptophan substitution at a position corresponding to position 577, in each case the position numbering is recited relative to the *Arabidopsis* residue numbering.

The term "nucleic acid" or "nucleic acid sequence" refers to an oligonucleotide, nucleotide or polynucleotide, and fragments or portions thereof, which may be single or double stranded, and represent the sense or antisense strand. A nucleic acid may include DNA or RNA, and may be of natural or synthetic origin. For example, a nucleic acid may include mRNA or cDNA. Nucleic acid may include nucleic acid that has been amplified (e.g., using polymerase chain reaction). The convention "NTwt###NTmut" is used to indicate a mutation that results in the wild-type nucleotide NTwt at position ### in the nucleic acid being replaced with mutant NTmut. The single letter code for nucleotides is as described in the U.S. Patent Office Manual of Patent Examining Procedure, section 2422, table 1. In this regard, the nucleotide designation "R" means purine such as guanine or adenine, "Y" means pyrimidine such as cytosine or thymine (uracil if RNA); "M" means adenine or cytosine; "K" means guanine or thymine; and "W" means adenine or thymine.

A "gene" refers to a DNA sequence that comprises control and coding sequences necessary for the production of an RNA, which may have a non-coding function (e.g., a ribosomal or transfer RNA) or which may include a polypeptide or a polypeptide precursor. The RNA or polypeptide may be encoded by a full length coding sequence or by any portion of the coding sequence so long as the desired activity or function is retained. As used herein, the term "AHAS Gene" refers to a gene that has 70%; 75%; 80%; 85%; 90%; 95%; 96%; 97%; 98%; 99%; or 100% identity to a Euphorbiaceae AHAS gene, for example the Cassava (*Manihot esculenta*) gene sequence of SEQ ID NO: 2. In certain embodiments, the AHAS gene has 60%; 70%; 75%; 80%; 85%; 90%; 95%; 96%; 97%; 98%; 99%; or 100% identity to SEQ ID NO: 2. In each case, the gene can comprise a mutation in the nucleotide sequence which results in a substitution at one or more amino acid positions, one of which corresponds to a W574S mutation.

By "coding sequence" is meant a sequence of a nucleic acid or its complement, or a part thereof, that can be transcribed and/or translated to produce the mRNA for and/or the polypeptide or a fragment thereof. Coding sequences include exons in a genomic DNA or immature primary RNA transcripts, which are joined together by the cell's biochemical machinery to provide a mature mRNA. The anti-sense strand is the complement of such a nucleic acid, and the encoding sequence can be deduced therefrom.

By "non-coding sequence" is meant a sequence of a nucleic acid or its complement, or a part thereof, that is not transcribed into amino acid in vivo, or where tRNA does not interact to place or attempt to place an amino acid. Non-coding sequences include both intron sequences in genomic DNA or immature primary RNA transcripts, and gene-associated sequences such as promoters, enhancers, silencers, etc.

A nucleobase is a base, which in certain preferred embodiments is a purine, pyrimidine, or a derivative or analog thereof. Nucleosides are nucleobases that contain a pentosefuranosyl moiety, e.g., an optionally substituted riboside or 2'-deoxyriboside. Nucleosides can be linked by one of several linkage moieties, which may or may not contain phosphorus. Nucleosides that are linked by unsubstituted phosphodiester linkages are termed nucleotides. The term "nucleobase" as used herein includes peptide nucleobases, the subunits of peptide nucleic acids, and morpholine nucleobases as well as nucleosides and nucleotides.

An oligonucleobase is a polymer comprising nucleobases; preferably at least a portion of which can hybridize by Watson-Crick base pairing to a DNA having the complementary sequence. An oligonucleobase chain may have a single 5' and 3' terminus, which are the ultimate nucleobases of the polymer. A particular oligonucleobase chain can contain nucleobases of all types. An oligonucleobase compound is a compound comprising one or more oligonucleobase chains that may be complementary and hybridized by Watson-Crick base pairing. Ribo-type nucleobases include pentosefuranosyl containing nucleobases wherein the 2' carbon is a methylene substituted with a hydroxyl, alkyloxy or halogen. Deoxyribo-type nucleobases are nucleobases other than ribo-type nucleobases and include all nucleobases that do not contain a pentosefuranosyl moiety.

In certain embodiments, an oligonucleobase strand may include both oligonucleobase chains and segments or regions of oligonucleobase chains. An oligonucleobase strand may have a 3' end and a 5' end, and when an oligonucleobase strand is coextensive with a chain, the 3' and 5' ends of the strand are also 3' and 5' termini of the chain.

The term "gene repair oligonucleobase" as used herein denotes oligonucleobases, including mixed duplex oligonucleotides, non-nucleotide containing molecules, single stranded oligodeoxynucleotides and other gene repair molecules.

By "isolated", when referring to a nucleic acid (e.g., an oligonucleotide such as RNA, DNA, or a mixed polymer) is meant a nucleic acid that is apart from a substantial portion of the genome in which it naturally occurs and/or is substantially separated from other cellular components which naturally accompany such nucleic acid. For example, any nucleic acid that has been produced synthetically (e.g., by serial base condensation) is considered to be isolated. Likewise, nucleic acids that are recombinantly expressed, cloned, produced by a primer extension reaction (e.g., PCR), or otherwise excised from a genome are also considered to be isolated.

An "amino acid sequence" refers to a polypeptide or protein sequence. The convention "AAwt###AAmut" is used to indicate a mutation that results in the wild-type amino acid AAwt at position ### in the polypeptide being replaced with mutant AAmut.

By "complement" is meant the complementary sequence to a nucleic acid according to standard Watson/Crick pairing rules. A complement sequence can also be a sequence of RNA complementary to the DNA sequence or its complement sequence, and can also be a cDNA.

By "substantially complementary" is meant that two sequences hybridize under stringent hybridization conditions. The skilled artisan will understand that substantially complementary sequences need not hybridize along their entire length.

As used herein the term "codon" refers to a sequence of three adjacent nucleotides (either RNA or DNA) constituting the genetic code that determines the insertion of a specific amino acid in a polypeptide chain during protein synthesis or the signal to stop protein synthesis. The term "codon" is also used to refer to the corresponding (and complementary) sequences of three nucleotides in the messenger RNA into which the original DNA is transcribed.

As used herein, the term "AHAS Protein" refers to a protein that has 70%; 75%; 80%; 85%; 90%; 95%; 96%; 97%; 98%; 99%; or 100% identity to a Euphorbiaceae AHAS protein, for example the Cassava (*Manihot esculenta*) protein sequence of SEQ ID NO: 1. In certain embodiments, the AHAS protein has 70%; 75%; 80%; 85%; 90%; 95%; 96%; 97%; 98%; 99%; or 100% identity to SEQ ID NO: 1. In each case, the gene can comprise a mutation at one or more amino acid positions, one of which corresponds to a W574S mutation. The term "AHAS Protein" also refers to a protein that has 70%; 75%; 80%; 85%; 90%; 95%; 96%; 97%; 98%; 99%; or 100% identity to a Euphorbiaceae AHAS protein, for example the Cassava (*Manihot esculenta*) protein sequence of SEQ ID NO: 1. In certain embodiments, the AHAS protein has 70%; 75%; 80%; 85%; 90%; 95%; 96%; 97%; 98%; 99%; or 100% identity to SEQ ID NO: 1. In each case, the gene can comprise a mutation at one or more amino acid positions, one of which corresponds to a D376A mutation The term "wild-type" refers to a gene or a gene product that has the characteristics of that gene or gene product when isolated from a naturally occurring source. A wild-type gene is that which is most frequently observed in a population and is thus arbitrarily designated the "normal" or "wild-type" form of the gene. "Wild-type" may also refer to the sequence at a specific nucleotide position or positions, or the sequence at a particular codon position or positions, or the sequence at a particular amino acid position or positions.

As used herein, "mutant," or "modified" refers to a nucleic acid or protein which displays modifications in sequence and or functional properties (i.e., altered characteristics) when compared to the wild-type gene or gene product. "Mutant," or "modified" also refers to the sequence at a specific nucleotide position or positions, or the sequence at a particular codon position or positions, or the sequence at a particular amino acid position or positions which displays modifications in sequence and or functional properties (i.e., altered characteristics) when compared to the wild-type gene or gene product.

A "mutation" is meant to encompass at least a single nucleotide variation in a nucleic acid sequence or a single amino acid variation in a polypeptide relative to the normal sequence or wild-type sequence. A mutation may include a substitution, a deletion, an inversion or an insertion.

As used herein, the term "homology" refers to sequence similarity among proteins and DNA. The term "homology" or "homologous" refers to a degree of identity. There may be partial homology or complete homology. A partially homologous sequence is one that has less than 100% sequence identity when compared to another sequence.

"Heterozygous" refers to having different alleles at one or more genetic loci in homologous chromosome segments. As used herein "heterozygous" may also refer to a sample, a cell, a cell population or an organism in which different alleles at one or more genetic loci may be detected. Heterozygous samples may also be determined via methods known in the art such as, for example, nucleic acid sequencing. For example, if a sequencing electropherogram shows two peaks at a single locus and both peaks are roughly the same size, the sample may be characterized as heterozygous. Or, if one peak is smaller than another, but is at least about 25% the size of the larger peak, the sample may be characterized as heterozygous. In some embodiments, the smaller peak is at least about 15% of the larger peak. In other embodiments, the smaller peak is at least about 10% of the larger peak. In other embodiments, the smaller peak is at least about 5% of the larger peak. In other embodiments, a minimal amount of the smaller peak is detected.

As used herein, "homozygous" refers to having identical alleles at one or more genetic loci in homologous chromosome segments. "Homozygous" may also refer to a sample, a cell, a cell population or an organism in which the same alleles at one or more genetic loci may be detected. Homozygous samples may be determined via methods known in the art, such as, for example, nucleic acid sequencing. For example, if a sequencing electropherogram shows a single peak at a particular locus, the sample may be termed "homozygous" with respect to that locus.

The term "hemizygous" refers to a gene or gene segment being present only once in the genotype of a cell or an organism because the second allele is deleted. As used herein "hemizygous" may also refer to a sample, a cell, a cell population or an organism in which an allele at one or more genetic loci may be detected only once in the genotype.

The term "zygosity status" as used herein refers to a sample, a cell population, or an organism as appearing heterozygous, homozygous, or hemizygous as determined by testing methods known in the art and described herein. The term "zygosity status of a nucleic acid" means determining whether the source of nucleic acid appears heterozygous, homozygous, or hemizygous. The "zygosity status" may refer to differences in a single nucleotide in a sequence. In some methods, the zygosity status of a sample with respect to a single mutation may be categorized as homozygous wild-type, heterozygous (i.e., one wild-type allele and one mutant allele), homozygous mutant, or hemizygous (i.e., a single copy of either the wild-type or mutant allele).

As used herein, the term "RTDS" refers to The Rapid Trait Development System™ (RTDS™) developed by Cibus.

RTDS is a site-specific gene modification system that is effective at making precise changes in a gene sequence without the incorporation of foreign genes or control sequences.

The term "about" as used herein means in quantitative terms plus or minus 10%. For example, "about 3%" would encompass 2.7-3.3% and "about 10%" would encompass 9-11%. Moreover, where "about" is used herein in conjunction with a quantitative term it is understood that in addition to the value plus or minus 10%, the exact value of the quantitative term is also contemplated and described. For example, the term "about 3%" expressly contemplates, describes and includes exactly 3%.

BRIEF DESCRIPTION OF THE FIGURES

FIG. 1 shows an amino acid sequence for a wild type Cassava (*Manihot esculenta*) AHAS protein (SEQ ID NO: 1). The position of D376 is shown as underlined italics. The position of W574 is shown as double underlined. As noted herein, the residue numbering convention is based on that of *Arabidopsis*.

FIG. 2 shows a nucleotide sequence encoding a wild type Cassava (*Manihot esculenta*) AHAS protein (SEQ ID NO: 2).

FIG. 3A shows an amino acid sequence for Cassava (*Manihot esculenta*) AHAS comprising a D376A mutation (SEQ ID NO: 5).

FIG. 3B shows an amino acid sequence for Cassava (*Manihot esculenta*) AHAS comprising a W574S mutation (SEQ ID NO: 3).

FIG. 4 shows an amino acid sequence for *Arabidopsis* AHAS I (SEQ ID NO: 4). The position of D376 is shown as underlined italics. The position of W574 is shown as double underlined.

DETAILED DESCRIPTION OF THE INVENTION

Figure 5:
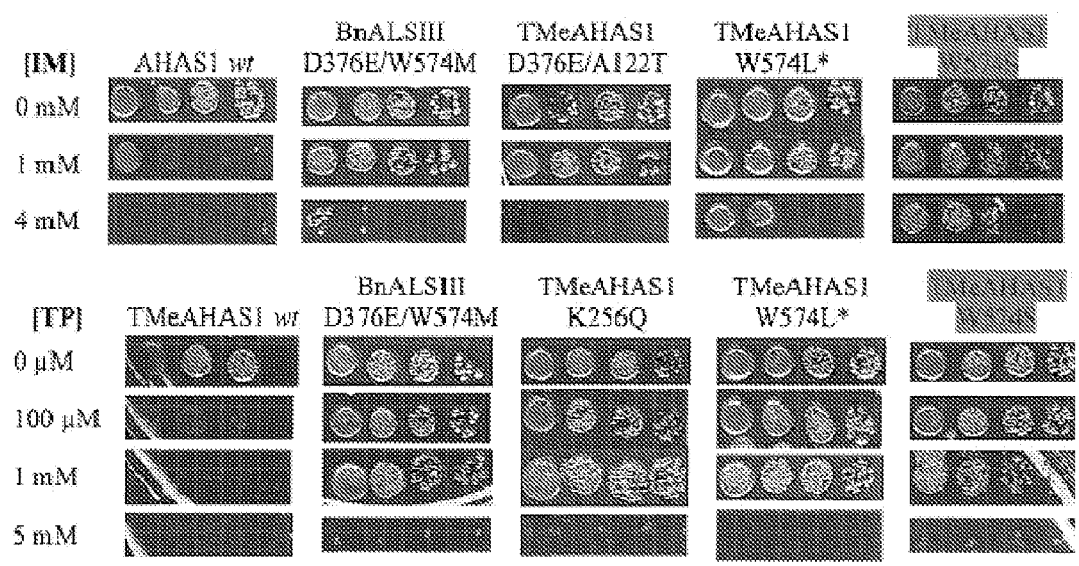
FIG. 5 shows growth on culture plates for CHI bacterial cells expressing various wild type and mutant AHAS proteins in the presence and absence of IM or TP herbicide, including the W574S mutant gene.

Provided are compositions and methods related in part to the successful targeting of acetohydroxyacid synthase (AHAS) genes in Euphorbiaceae using, for example, the Rapid Trait Development System (RTDS™) technology developed by Cibus. In combination or alone, plants containing any of the mutations disclosed herein can form the basis of new herbicide-resistant products. Also provided are seeds produced from the mutated plants in which the AHAS genes are either homozygous or heterozygous for the mutations. The mutations disclosed herein can be in combination with any other mutation known or with mutations discovered in the future.

RTDS is based on altering a targeted gene by utilizing the cell's own gene repair system to specifically modify the gene sequence in situ and not insert foreign DNA and gene expression control sequences. This procedure effects a precise change in the genetic sequence while the rest of the genome is left unaltered. In contrast to conventional transgenic GMOs, there is no integration of foreign genetic material, nor is any foreign genetic material left in the plant. The changes in the genetic sequence introduced by RTDS are not randomly inserted. Since affected genes remain in their native location, no random, uncontrolled or adverse pattern of expression occurs.

The RTDS that effects this change is a chemically synthesized oligonucleotide which may be composed of both DNA and modified RNA bases as well as other chemical moieties, and is designed to hybridize at the targeted gene location to create a mismatched base-pair(s). This mismatched base-pair acts as a signal to attract the cell's own natural gene repair system to that site and correct (replace, insert or delete) the designated nucleotide(s) within the gene. Once the correction process is complete the RTDS molecule is degraded and the now-modified or repaired gene is expressed under that gene's normal endogenous control mechanisms.

The introduction of exogenous mutant genes into plants is well documented. For example, U.S. Pat. No. 4,545,060 relates to increasing a plant's resistance to glyphosate by introducing into the plant's genome a gene coding for an EPSPS variant having at least one mutation that renders the enzyme more resistant to its competitive inhibitor, i.e., glyphosate.

Examples of some of the mutations in AHAS genes are known. See e.g. U.S. Pat. No. 7,094,606.

Through chemical mutagenesis, a mutation was found in the lower expressed AHAS I gene. This mutation is known as PM-1 (a mutation at an equivalent position known as 653 based on the acetolactate synthase (ALS) amino acid sequence of *Arabidopsis*, a serine to asparagine amino acid change, respectively encoded as follows—AGT to AAT). Another mutation was found in the higher expressed gene AHAS III, known as PM-2 (a mutation at an equivalent position known as 574, a tryptophan to leucine amino acid change, respectively encoded as follows—TGG to TTG). These two mutations, PM-1 and PM-2, are combined in a commercial variety of Canola known as Clearfield Canola (Tan et al., 2005).

For exemplary purposes, the subject mutations are depicted in Cassava (*Manihot esculenta*). The compositions and methods also encompass mutant AHAS genes of other Euphorbiaceae species (paralogs). However, due to variations in the AHAS genes of different species, the number of the amino acid residue to be changed in one species may be different in another species. Nevertheless, the analogous position is readily identified by one of skill in the art by sequence homology.

The compositions and methods relate in part to mutations in an AHAS gene that render a plant resistant or tolerant to an herbicide of the AHAS-inhibiting or ALS-inhibiting family of herbicides. The compositions and methods also relate to the use of a gene repair oligonucleobase to make a desired mutation in the chromosomal or episomal sequences of a plant in the gene encoding for an AHAS protein. The mutated protein, which substantially maintains the catalytic activity of the wild-type protein, allows for increased resistance or tolerance of the plant to an herbicide of the AHAS-inhibiting family, and allows for the substantially normal growth or development of the plant, its organs, tissues, or cells as compared to the wild-type plant irrespective of the presence or absence of the herbicide. The compositions and methods also relate to a non-transgenic plant cell in which an AHAS gene has been mutated, a non-transgenic plant regenerated therefrom, as well as a plant resulting from a cross using a regenerated non-transgenic plant to a plant having a mutation in a different AHAS gene or to a plant having a mutated EPSPS gene, for example.

Imidazolinones are among the five chemical families of AHAS-inhibiting herbicides. The other four families are sulfonylureas, triazolopyrimidines, pyrimidinylthiobenzoates and sulfonylamino-carbonyltriazolinones (Tan et al., 2005).

Also provided is a transgenic or non-transgenic plant or plant cell having one or more mutations in the AHAS gene, for example, such as disclosed herein. In certain embodiments, the plant or plant cell having one or more mutations in the AHAS gene has increased resistance or tolerance to a member of the AHAS-inhibiting. In certain embodiments, the plant or plant cell having one or more mutations in the AHAS gene may exhibit substantially normal growth or development of the plant, its organs, tissues or cells, as compared to the corresponding wild-type plant or cell. In particular aspects and embodiments provided are non-transgenic plants having a mutation in an AHAS gene, for example, such as disclosed herein, which in certain embodiments has increased resistance or tolerance to a member of the AHAS-inhibiting herbicide family and may exhibit substantially normal growth or development of the plant, its organs, tissues or cells, as compared to the corresponding wild-type plant or cell, i.e., in the presence of one or more herbicide such as for example, an imidazolinone and/or sulfonylurea, the mutated AHAS protein has substantially the same catalytic activity as compared to the wild-type AHAS protein.

Further provided are methods for producing a plant having a mutated AHAS gene, for example, having one or more mutations as described herein; preferably the plant substantially maintains the catalytic activity of the wild-type protein irrespective of the presence or absence of a relevant herbicide. In certain embodiments, the methods include introducing into a plant cell a gene repair oligonucleobase with one or more targeted mutations in the AHAS gene (for example, such as disclosed herein) and identifying a cell, seed, or plant having a mutated AHAS gene.

The gene repair oligonucleobase can be introduced into a plant cell using any method commonly used in the art, including but not limited to, microcarriers (biolistic delivery), microfibers, polyethylene glycol (PEG)-mediated uptake, electroporation, and microinjection.

Also provided are methods and compositions related to the culture of cells mutated according to methods as disclosed herein in order to obtain a plant that produces seeds, henceforth a "fertile plant", and the production of seeds and additional plants from such a fertile plant.

Also provided are methods of selectively controlling weeds in a field, the field comprising plants with the disclosed AHAS gene alterations and weeds, the method comprising application to the field of an herbicide to which the plants have been rendered resistant.

Also provided are mutations in the AHAS gene that confer resistance or tolerance to a member of the relevant herbicide to a plant or wherein the mutated AHAS gene has substantially the same enzymatic activity as compared to wild-type AHAS.

Gene Repair Oligonucleobases

The methods and compositions disclosed herein can be practiced or made with "gene repair oligonucleobases" having the conformations and chemistries as described in detail below. The "gene repair oligonucleobases" as contemplated herein have also been described in published scientific and patent literature using other names including "recombinagenic oligonucleobases;" "RNA/DNA chimeric oligonucleotides;" "chimeric oligonucleotides;" "mixed duplex oligonucleotides" (MDONs); "RNA DNA oligonucleotides (RDOs);" "gene targeting oligonucleotides;" "genoplasts;" "single stranded modified oligonucleotides;" "Single stranded oligodeoxynucleotide mutational vectors" (SSOMVs); "duplex mutational vectors;" and "heteroduplex mutational vectors."

Oligonucleobases having the conformations and chemistries described in U.S. Pat. No. 5,565,350 by Kmiec (Kmiec I) and U.S. Pat. No. 5,731,181 by Kmiec (Kmiec II), hereby incorporated by reference, are suitable for use as "gene repair oligonucleobases" of the invention. The gene repair oligonucleobases in Kmiec I and/or Kmiec II contain two complementary strands, one of which contains at least one segment of RNA-type nucleotides (an "RNA segment") that are base paired to DNA-type nucleotides of the other strand.

Kmiec II discloses that purine and pyrimidine base-containing non-nucleotides can be substituted for nucleotides. Additional gene repair molecules that can be used for the present invention are described in U.S. Pat. Nos. 5,756,325; 5,871,984; 5,760,012; 5,888,983; 5,795,972; 5,780,296; 5,945,339; 6,004,804; and 6,010,907 and in International Patent No. PCT/US00/23457; and in International Patent Publication Nos. WO 98/49350; WO 99/07865; WO 99/58723; WO 99/58702; and WO 99/40789, which are each hereby incorporated in their entirety.

In one embodiment, the gene repair oligonucleobase is a mixed duplex oligonucleotides (MDON) in which the RNA-type nucleotides of the mixed duplex oligonucleotide are made RNase resistant by replacing the 2'-hydroxyl with a fluoro, chloro or bromo functionality or by placing a substituent on the 2'-O. Suitable substituents include the substituents taught by the Kmiec II. Alternative substituents include the substituents taught by U.S. Pat. No. 5,334,711 (Sproat) and the substituents taught by patent publications EP 629 387 and EP 679 657 (collectively, the Martin Applications), which are hereby incorporated by reference. As used herein, a 2'-fluoro, chloro or bromo derivative of a ribonucleotide or a ribonucleotide having a 2'-OH substituted with a substituent described in the Martin Applications or Sproat is termed a "2'-Substituted Ribonucleotide." As used herein the term "RNA-type nucleotide" means a 2'-hydroxyl or 2'-Substituted Nucleotide that is linked to other nucleotides of a mixed duplex oligonucleotide by an unsubstituted phosphodiester linkage or any of the non-natural linkages taught by Kmiec I or Kmiec II. As used herein the term "deoxyribo-type nucleotide" means a nucleotide having a 2'-H, which can be linked to other nucleotides of a gene repair oligonucleobase by an unsubstituted phosphodiester linkage or any of the non-natural linkages taught by Kmiec I or Kmiec II.

In a particular embodiment of the present invention, the gene repair oligonucleobase is a mixed duplex oligonucleotides (MDON) that is linked solely by unsubstituted phosphodiester bonds. In alternative embodiments, the linkage is by substituted phosphodiesters, phosphodiester derivatives and non-phosphorus-based linkages as taught by Kmiec II. In yet another embodiment, each RNA-type nucleotide in the mixed duplex oligonucleotide is a 2'-Substituted Nucleotide. Particular preferred embodiments of 2'-Substituted Ribonucleotides are 2'-fluoro, 2'-methoxy, 2'-propyloxy, 2'-allyloxy, 2'-hydroxylethyloxy, 2'-methoxyethyloxy, 2'-fluoropropyloxy and 2'-trifluoropropyloxy substituted ribonucleotides. More preferred embodiments of 2'-Substituted Ribonucleotides are 2'-fluoro, 2'-methoxy, 2'-methoxyethyloxy, and 2'-allyloxy substituted nucleotides. In another embodiment the mixed duplex oligonucleotide is linked by unsubstituted phosphodiester bonds.

Although mixed duplex oligonucleotides (MDONs) having only a single type of 2'-substituted RNA-type nucleotide are more conveniently synthesized, the methods of the invention can be practiced with mixed duplex oligonucleotides having two or more types of RNA-type nucleotides. The function of an RNA segment may not be affected by an interruption caused by the introduction of a deoxynucleotide between two RNA-type trinucleotides, accordingly, the term RNA segment encompasses terms such as "interrupted RNA segment." An uninterrupted RNA segment is termed a contiguous RNA segment. In an alternative embodiment an RNA segment can contain alternating RNase-resistant and unsubstituted 2'-OH nucleotides. The mixed duplex oligonucleotides preferably have fewer than 100 nucleotides and more preferably fewer than 85 nucleotides, but more than 50 nucleotides. The first and second strands are Watson-Crick base paired. In one embodiment the strands of the mixed duplex oligonucleotide are covalently bonded by a linker, such as a single stranded hexa, penta or tetranucleotide so that the first and second strands are segments of a single oligonucleotide chain having a single 3' and a single 5' end. The 3' and 5' ends can be protected by the addition of a "hairpin cap" whereby the 3' and 5' terminal nucleotides are Watson-Crick paired to adjacent nucleotides. A second hairpin cap can, additionally, be placed at the junction between the first and second strands distant from the 3' and 5' ends, so that the Watson-Crick pairing between the first and second strands is stabilized.

The first and second strands contain two regions that are homologous with two fragments of the target gene, i.e., have the same sequence as the target gene. A homologous region contains the nucleotides of an RNA segment and may contain one or more DNA-type nucleotides of connecting DNA segment and may also contain DNA-type nucleotides that are not within the intervening DNA segment. The two regions of homology are separated by, and each is adjacent to, a region having a sequence that differs from the sequence of the target gene, termed a "heterologous region." The heterologous region can contain one, two or three mismatched nucleotides. The mismatched nucleotides can be contiguous or alternatively can be separated by one or two nucleotides that are homologous with the target gene. Alternatively, the heterologous region can also contain an insertion or one, two, three or of five or fewer nucleotides. Alternatively, the sequence of the mixed duplex oligonucleotide may differ from the sequence of the target gene only by the deletion of one, two, three, or five or fewer nucleotides from the mixed duplex oligonucleotide. The length and position of the heterologous region is, in this case, deemed to be the length of the deletion, even though no nucleotides of the mixed duplex oligonucleotide are within the heterologous region. The distance between the fragments of the target gene that are complementary to the two homologous regions is identical to the length of the heterologous region where a substitution or substitutions is intended. When the heterologous region contains an insertion, the homologous regions are thereby separated in the mixed duplex oligonucleotide farther than their complementary homologous fragments are in the gene, and the converse is applicable when the heterologous region encodes a deletion.

The RNA segments of the mixed duplex oligonucleotides are each a part of a homologous region, i.e., a region that is identical in sequence to a fragment of the target gene, which segments together preferably contain at least 13 RNA-type nucleotides and preferably from 16 to 25 RNA-type nucleotides or yet more preferably 18-22 RNA-type nucleotides or most preferably 20 nucleotides. In one embodiment, RNA segments of the homology regions are separated by and adjacent to, i.e., "connected by" an intervening DNA segment. In one embodiment, each nucleotide of the heterologous region is a nucleotide of the intervening DNA segment. An intervening DNA segment that contains the heterologous region of a mixed duplex oligonucleotide is termed a "mutator segment."

In another embodiment of the present invention, the gene repair oligonucleobase (GRON) is a single stranded oligodeoxynucleotide mutational vector (SSOMV), which is disclosed in International Patent Application PCT/US00/23457, U.S. Pat. Nos. 6,271,360, 6,479,292, and 7,060,500 which is incorporated by reference in its entirety. The sequence of the SSOMV is based on the same principles as the mutational vectors described in U.S. Pat. Nos. 5,756,325; 5,871,984; 5,760,012; 5,888,983; 5,795,972; 5,780,296; 5,945,339; 6,004,804; and 6,010,907 and in International Publication Nos. WO 98/49350; WO 99/07865; WO 99/58723; WO 99/58702; and WO 99/40789. The sequence of the SSOMV contains two regions that are homologous with the target sequence separated by a region that contains the desired genetic alteration termed the mutator region. The mutator region can have a sequence that is the same length as the sequence that separates the homologous regions in the target sequence, but having a different sequence. Such a mutator region can cause a substitution. Alternatively, the homologous regions in the SSOMV can be contiguous to each other, while the regions in the target gene having the same sequence are separated by one, two or more nucleotides. Such an SSOMV causes a deletion from the target gene of the nucleotides that are absent from the SSOMV. Lastly, the sequence of the target gene that is identical to the homologous regions may be adjacent in the target gene but separated by one, two, or more nucleotides in the sequence of the SSOMV. Such an SSOMV causes an insertion in the sequence of the target gene.

The nucleotides of the SSOMV are deoxyribonucleotides that are linked by unmodified phosphodiester bonds except that the 3' terminal and/or 5' terminal internucleotide linkage or alternatively the two 3' terminal and/or 5' terminal internucleotide linkages can be a phosphorothioate or phosphoamidate. As used herein an internucleotide linkage is the linkage between nucleotides of the SSOMV and does not include the linkage between the 3' end nucleotide or 5' end nucleotide and a blocking substituent. In a specific embodiment the length of the SSOMV is between 21 and 55 deoxynucleotides and the lengths of the homology regions are, accordingly, a total length of at least 20 deoxynucleotides and at least two homology regions should each have lengths of at least 8 deoxynucleotides.

The SSOMV can be designed to be complementary to either the coding or the non-coding strand of the target gene. When the desired mutation is a substitution of a single base, it is preferred that both the mutator nucleotide and the targeted nucleotide be a pyrimidine. To the extent that is consistent with achieving the desired functional result, it is preferred that both the mutator nucleotide and the targeted nucleotide in the complementary strand be pyrimidines. Particularly preferred are SSOMVs that encode transversion mutations, i.e., a C or T mutator nucleotide is mismatched, respectively, with a C or T nucleotide in the complementary strand.

In addition to the oligodeoxynucleotide, the SSOMV can contain a 5' blocking substituent that is attached to the 5' terminal carbons through a linker. The chemistry of the linker is not critical other than its length, which should preferably be at least 6 atoms long and that the linker should be flexible. A variety of non-toxic substituents such as biotin, cholesterol or other steroids or a non-intercalating cationic fluorescent dye can be used. Particularly preferred reagents to make SSOMVs are the reagents sold as Cy3™ and Cy5™ by Glen Research, Sterling Va. (now GE Healthcare), which are blocked phosphoroamidites that upon incorporation into an oligonucleotide yield 3,3,3',3'-tetramethyl N,N'-isopropyl substituted indomonocarbocyanine and indodicarbocyanine dyes, respectively. Cy3 is particularly preferred. When the indocarbocyanine is N-oxyalkyl substituted it can be conveniently linked to the 5' terminal of the oligodeoxynucleotide as a phosphodiester with a 5' terminal phosphate. The chemistry of the dye linker between the dye and the oligodeoxynucleotide is not critical and is chosen for synthetic convenience. When the commercially available Cy3 phosphoramidite is used as directed, the resulting 5' modification consists of a blocking substituent and linker together which are a N-hydroxypropyl, N'-phosphatidylpropyl 3,3,3',3'-tetramethyl indomonocarbocyanine.

In a preferred embodiment the indocarbocyanine dye is tetra substituted at the 3 and 3' positions of the indole rings. Without limitations as to theory these substitutions prevent the dye from being an intercalating dye. The identity of the substituents at these positions is not critical. The SSOMV can in addition have a 3' blocking substituent. Again the chemistry of the 3' blocking substituent is not critical.

The mutations herein described might also be obtained by mutagenesis (random, somatic or directed) and other DNA editing or recombination technologies including, but not limited to, gene targeting using site-specific homologous recombination by zinc finger nucleases.

Increasing Efficiency of Targeted Gene Modification

Nucleic acids which direct specific changes to the genome may be combined with various approaches to enhance the availability of components of the natural repair systems present in the cells being targeted for modification. These approaches include, but are not limited to, the use of Transcription Activator-Like Effector Nucleases (TALENs) or Clustered Regularly Interspaced Short Palindromic Repeats (CRISPRs). See, e.g., WO2014/144951 and WO2014/144951, the contents of each of which are hereby incorporated by reference.

TALENs are targetable nucleases are used to induce single- and double-strand breaks into specific DNA sites, which are then repaired by mechanisms that can be exploited to create sequence alterations at the cleavage site. The fundamental building block that is used to engineer the DNA-binding region of TALENs is a highly conserved repeat domain derived from naturally occurring TALEs encoded by *Xanthomonas* spp. proteobacteria. DNA binding by a TALEN is mediated by arrays of highly conserved 33-35 amino acid repeats that are flanked by additional TALE-derived domains at the amino-terminal and carboxy-terminal ends of the repeats. These TALE repeats specifically bind to a single base of DNA, the identity of which is determined by two hypervariable residues typically found at positions 12 and 13 of the repeat, with the number of repeats in an array corresponded to the length of the desired target nucleic acid, the identity of the repeat selected to match the target nucleic acid sequence. The target nucleic acid is preferably between 15 and 20 base pairs in order to maximize selectivity of the target site. Cleavage of the target nucleic acid typically occurs within 50 base pairs of TALEN binding. Computer programs for TALEN recognition site design have been described in the art. See, e.g., Cermak et al., Nucleic Acids Res. 2011 July; 39(12): e82. Once designed to match the desired target sequence, TALENS can be expressed recombinantly and introduced into protoplasts as exogenous proteins, or expressed from a plasmid within the protoplast.

Similarly, the CRISPR/Cas system can be used for gene editing. By delivering the Cas9 or other CRISPR-associated protein and appropriate guide RNAs (gRNAs) into a cell, the organism's genome can be cut at any desired location. The gRNA/Cas9 complex is recruited to the target sequence by the base-pairing between the gRNA sequence and the complement to the target sequence in the genomic DNA. For successful binding of Cas9, the genomic target sequence must also contain the correct Protospacer Adjacent Motif (PAM) sequence immediately following the target sequence. The binding of the gRNA/Cas9 complex localizes the Cas9 to the genomic target sequence so that the wild-type Cas9 can cut both strands of DNA causing a Double Strand Break (DSB). Cas9 will cut 3-4 nucleotides upstream of the PAM sequence. A DSB can be repaired through one of two general repair pathways: (1) the Non-Homologous End Joining (NHEJ) DNA repair pathway or (2) the Homology Directed Repair (HDR) pathway. The HDR pathway utilizes a repair template to fix the DSB. HDR faithfully copies the sequence of the repair template to the cut target sequence. Specific nucleotide changes can be introduced into a targeted gene by the use of HDR with a repair template to edit a gene.

Another class of artificial endonucleases is the engineered meganucleases. Engineered homing endonucleases are generated by modifying the specificity of existing homing endonucleases. In one approach, variations are introduced in the amino acid sequence of naturally occurring homing endonucleases and then the resultant engineered homing endonucleases are screened to select functional proteins which cleave a targeted binding site. In another approach, chimeric homing endonucleases are engineered by combining the recognition sites of two different homing endonucleases to create a new recognition site composed of a half-site of each homing endonuclease.

Delivery of Gene Repair Oligonucleobases into Plant Cells

Any commonly known method used to transform a plant cell can be used for delivering the gene repair oligonucleobases. Illustrative methods are listed below.

Microcarriers and Microfibers

The use of metallic microcarriers (microspheres) for introducing large fragments of DNA into plant cells having cellulose cell walls by projectile penetration is well known to those skilled in the relevant art (henceforth biolistic delivery). U.S. Pat. Nos. 4,945,050; 5,100,792 and 5,204,253 describe general techniques for selecting microcarriers and devices for projecting them.

Specific conditions for using microcarriers in the methods of the present invention are described in International Publication WO 99/07865. In an illustrative technique, ice cold microcarriers (60 mg/mL), mixed duplex oligonucleotide (60 mg/mL) 2.5 M CaCl$_2$ and 0.1 M spermidine are added in that order; the mixture gently agitated, e.g., by vortexing, for 10 minutes and then left at room temperature for 10 minutes, whereupon the microcarriers are diluted in 5 volumes of ethanol, centrifuged and resuspended in 100% ethanol. Good results can be obtained with a concentration in the adhering solution of 8-10 µg/µL microcarriers, 14-17 µg/mL mixed duplex oligonucleotide, 1.1-1.4 M CaCl$_2$ and 18-22 mM spermidine. Optimal results were observed under the conditions of 8 µg/µL microcarriers, 16.5 µg/mL mixed duplex oligonucleotide, 1.3 M CaCl$_2$ and 21 mM spermidine.

Gene repair oligonucleobases can also be introduced into plant cells for the practice of the present invention using microfibers to penetrate the cell wall and cell membrane. U.S. Pat. No. 5,302,523 to Coffee et al. describes the use of 30.times.0.5 µm and 10.times.0.3 µm silicon carbide fibers to facilitate transformation of suspension maize cultures of Black Mexican Sweet. Any mechanical technique that can be used to introduce DNA for transformation of a plant cell using microfibers can be used to deliver gene repair oligonucleobases for transmutation.

An illustrative technique for microfiber delivery of a gene repair oligonucleobase is as follows: Sterile microfibers (2 µg) are suspended in 150 µL of plant culture medium containing about 10 µg of a mixed duplex oligonucleotide. A suspension culture is allowed to settle and equal volumes of packed cells and the sterile fiber/nucleotide suspension are vortexed for 10 minutes and plated. Selective media are applied immediately or with a delay of up to about 120 h as is appropriate for the particular trait.

Protoplast Electroporation

In an alternative embodiment, the gene repair oligonucleobases can be delivered to the plant cell by electroporation of a protoplast derived from a plant part. The protoplasts are formed by enzymatic treatment of a plant part, particularly a leaf, according to techniques well known to those skilled in the art. See, e.g., Gallois et al., 1996, in Methods in Molecular Biology 55:89-107, Humana Press, Totowa, N.J.; Kipp et al., 1999, in Methods in Molecular Biology 133: 213-221, Humana Press, Totowa, N.J. The protoplasts need not be cultured in growth media prior to electroporation. Illustrative conditions for electroporation are 3.times.10.sup.5 protoplasts in a total volume of 0.3 mL with a concentration of gene repair oligonucleobase of between 0.6-4 µg/mL.

Protoplast PEG-Mediated DNA Uptake

In an alternative embodiment, nucleic acids are taken up by plant protoplasts in the presence of the membrane-modifying agent polyethylene glycol, according to techniques well known to those skilled in the art (see, e.g., Gharti-Chhetri et al., 1992; Datta et al., 1992).

Microinjection

In an alternative embodiment, the gene repair oligonucleobases can be delivered by injecting it with a microcapillary into plant cells or into protoplasts (see, e.g., Miki et al., 1989; Schnorf et al., 1991).

Selection of Herbicide Resistant Plants and Application of Herbicide

Plants and plant cells can be tested for resistance or tolerance to an herbicide using commonly known methods in the art, e.g., by growing the plant or plant cell in the presence of an herbicide and measuring the rate of growth as compared to the growth rate in the absence of the herbicide.

As used herein, substantially normal growth of a plant, plant organ, plant tissue or plant cell is defined as a growth rate or rate of cell division of the plant, plant organ, plant tissue, or plant cell that is at least 35%, at least 50%, at least 60%, or at least 75% of the growth rate or rate of cell division in a corresponding plant, plant organ, plant tissue or plant cell expressing the wild-type AHAS protein.

As used herein, substantially normal development of a plant, plant organ, plant tissue or plant cell is defined as the occurrence of one or more development events in the plant, plant organ, plant tissue or plant cell that are substantially the same as those occurring in a corresponding plant, plant organ, plant tissue or plant cell expressing the wild-type AHAS protein.

In certain embodiments plant organs provided herein include, but are not limited to, leaves, stems, roots, vegetative buds, floral buds, meristems, embryos, cotyledons, endosperm, sepals, petals, pistils, carpels, stamens, anthers, microspores, pollen, pollen tubes, ovules, ovaries and fruits, or sections, slices or discs taken therefrom. Plant tissues include, but are not limited to, callus tissues, ground tissues, vascular tissues, storage tissues, meristematic tissues, leaf tissues, shoot tissues, root tissues, gall tissues, plant tumor tissues, and reproductive tissues. Plant cells include, but are not limited to, isolated cells with cell walls, variously sized aggregates thereof, and protoplasts.

Plants are substantially "tolerant" to a relevant herbicide when they are subjected to it and provide a dose/response curve which is shifted to the right when compared with that provided by similarly subjected non-tolerant like plant. Such dose/response curves have "dose" plotted on the X-axis and "percentage kill", "herbicidal effect", etc., plotted on the y-axis. Tolerant plants will require more herbicide than non-tolerant like plants in order to produce a given herbicidal effect. Plants that are substantially "resistant" to the herbicide exhibit few, if any, necrotic, lytic, chlorotic or other lesions, when subjected to herbicide at concentrations and rates which are typically employed by the agrochemical community to kill weeds in the field. Plants which are resistant to an herbicide are also tolerant of the herbicide.

EXAMPLES

Following are examples, which illustrate procedures for practicing the invention. These examples should not be construed as limiting. All percentages are by weight and all solvent mixture proportions are by volume unless otherwise noted.

Example 1: Preparation of Herbicide-Resistant Euphorbiaceae Samples

Unless otherwise specified, as used herein, numbering of the gene(s) is based on the amino acid sequence of the *Arabidopsis* acetolactate synthase (ALS) or acetohydroxyacid synthase (AHAS) At3g48560 (SEQ ID NO:4). In references prior to October 2005, the S653 position (based on the *Arabidopsis* amino acid sequence) is referred to as S621 based on the corn amino acid sequences ZmAHAS108 and ZmAHAS109 (Fang et al., 1992).

Mutations were generated by site-directed mutagenesis (SDM) of the wild-type Cassava AHAS gene 1 and transformed into CHI bacterial cells lacking the endogenous AHAS homolog. Serially-diluted cells were plated onto plates with increasing concentrations of either imazamox (IM) or flumetsulam (TP). Cassava AHAS wt and a canola ALS mutant known to be highly herbicide tolerant were used as negative and positive controls, respectively. The results are shown in FIG. 5. Representative set of bacterial spot tests showing the positive and negative controls, some other mutants tested and the W574S mutant. The herbicide concentrations listed on the left-most column correspond to the entire row and columns separate different lines. Each spot test consists of four 1:10 serial dilutions (10-3, 10-4, 10-5 and 10-6) after normalization based on the OD600 of each M9 liquid culture.

Cells with the negative control wt cassava AHAS gene grew on plates with no herbicide, but failed to grow on plates containing either the IM or TP herbicide. Positive control cells with the canola ALS mutant grew on all concentrations of IM and TP, until all growth ceased at 5 mM IM or TP.

Cells with the cassava W574S mutant display robust growth on both IM and TP containing plates that was similar to the canola positive control.

Figure 6A:
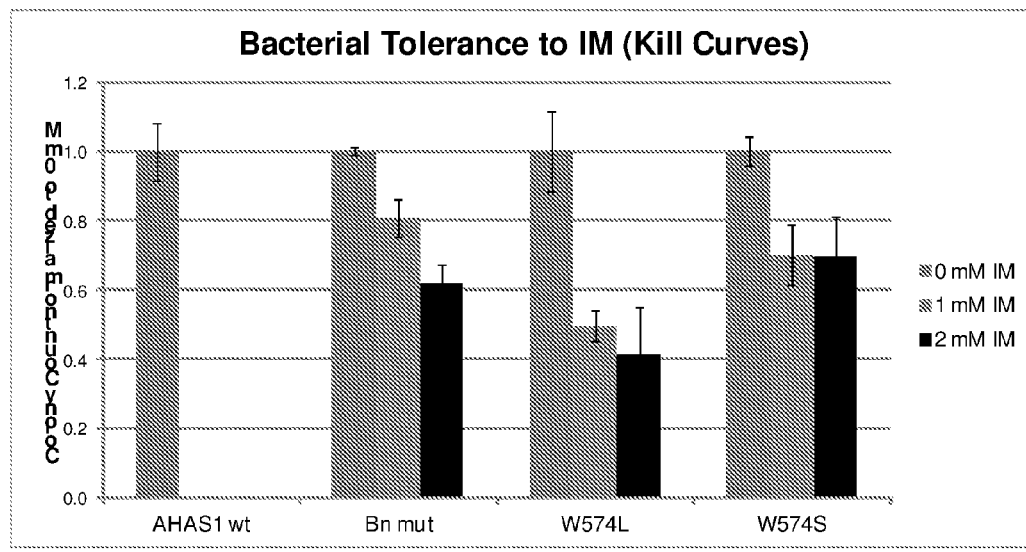
FIG. 6A shows IM herbicide kill curves for CHI bacterial cells expressing various wild type and mutant AHAS proteins, including the W574S mutant gene.
Figure 6B:
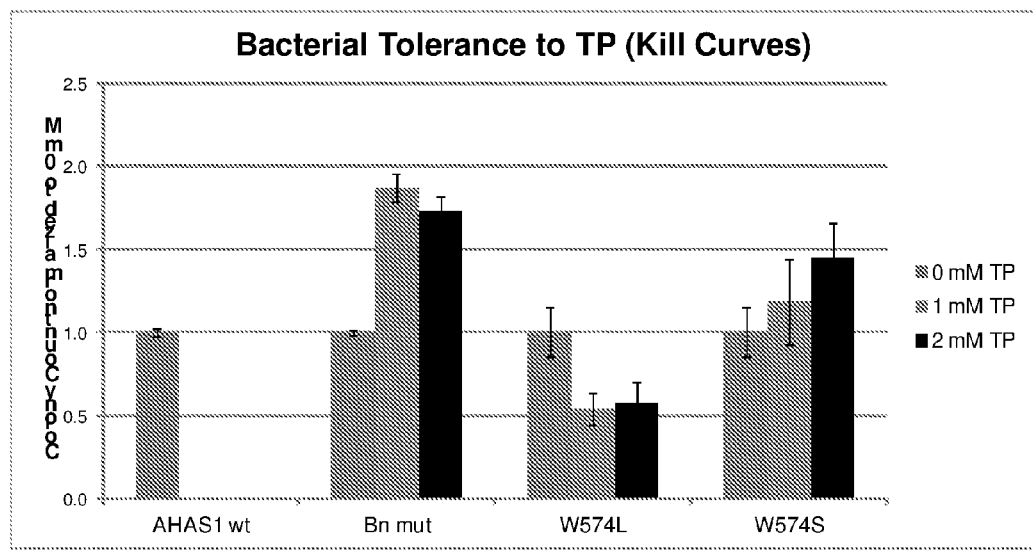
FIG. 6B shows TP herbicide kill curves for CHI bacterial cells expressing various wild type and mutant AHAS proteins, including the W574S mutant gene.

Mutants were also tested using a "kill curve" assay where equal numbers of cells containing the mutant of interest were plated onto plates with increasing concentrations of herbicide and the number of resulting colonies counted. Kill curve results averaged between three experiments, each with an average of three technical replicates. Error bars are ±one standard deviation of the averaged data. Results are depicted in FIG. 6. W574S, and its enhanced tolerance to the TP class of herbicides, has not previously been demonstrated in the art. W574L also has robust tolerance to both TP and IM, although growth is inconsistent.

Example 2: Preparation of Herbicide-Resistant Euphorbiaceae Samples

Figure 7:
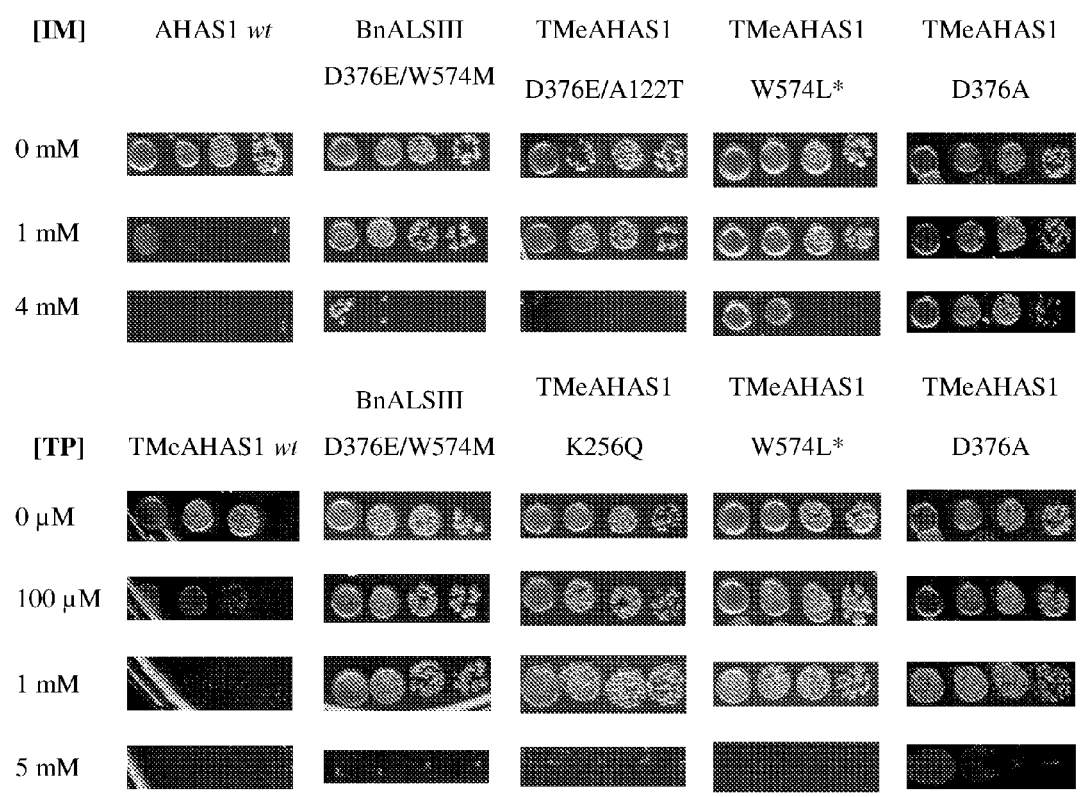
FIG. 7 shows growth on culture plates for CHI bacterial cells expressing various wild type and mutant AHAS proteins in the presence and absence of IM or TP herbicide, including the D376A mutant gene.

Mutations were generated by site-directed mutagenesis (SDM) of the wild-type Cassava AHAS gene 1 and transformed into CHI bacterial cells lacking the endogenous AHAS homolog. Serially-diluted cells were plated onto plates with increasing concentrations of either imazamox (IM) or flumetsulam (TP). Cassava AHAS wt and a canola ALS mutant known to be highly herbicide tolerant were used as negative and positive controls, respectively. The results are shown in FIG. 7. Representative set of bacterial spot tests showing the positive and negative controls, some other mutants tested and the D376A mutant. The herbicide concentrations listed on the left-most column correspond to the entire row and columns separate different lines. Each spot test consists of four 1:10 serial dilutions (10-3, 10-4, 10-5 and 10-6) after normalization based on the OD600 of each M9 liquid culture.

Cells with the negative control wt cassava AHAS gene grew on plates with no herbicide, but failed to grow on plates containing either the IM or TP herbicide. Positive control cells with the canola ALS mutant grew on all concentrations of IM and TP, until all growth ceased at 5 mM IM or TP.

D376A, and its robust tolerance to IM, is surprising as this has not been described in cassava to date. W574L also has robust tolerance to both TP and IM, although growth is inconsistent.

Figure 8A:
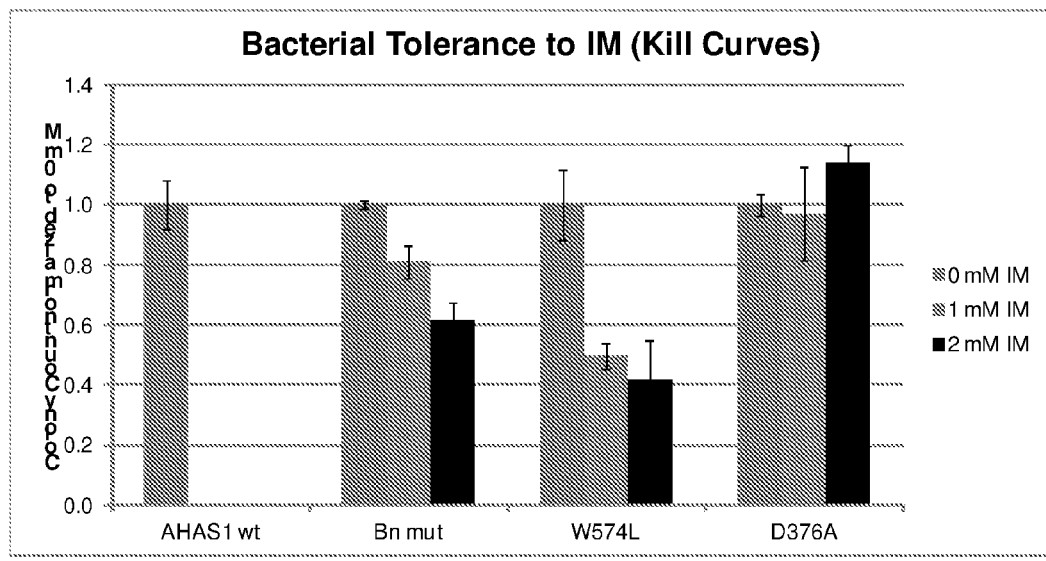
FIG. 8A shows IM herbicide kill curves for CHI bacterial cells expressing various wild type and mutant AHAS proteins.
Figure 8B:
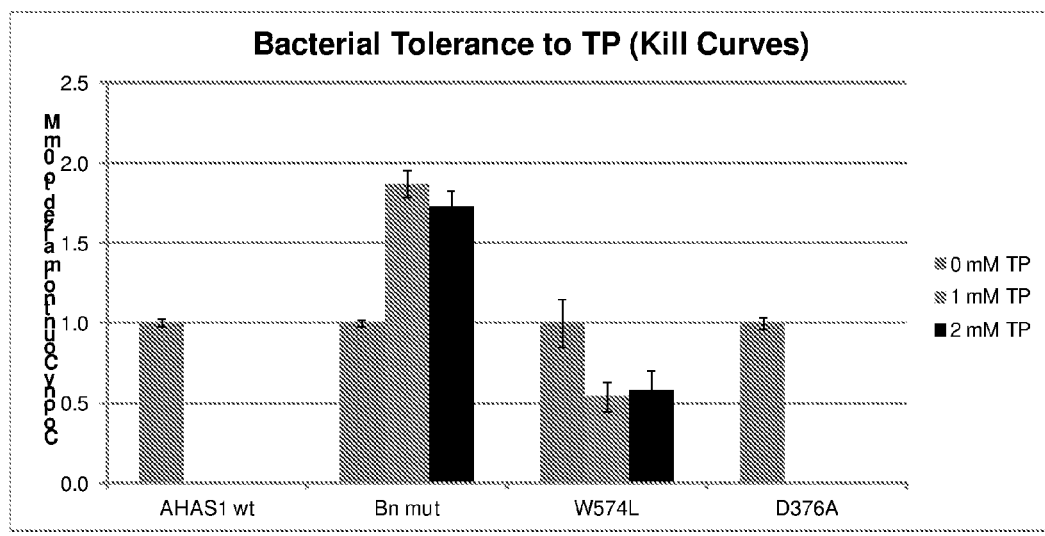
FIG. 8B shows TP herbicide kill curves for CHI bacterial cells expressing various wild type and mutant AHAS proteins.

Mutants were also tested using a "kill curve" assay where equal numbers of cells containing the mutant of interest were plated onto plates with increasing concentrations of herbicide and the number of resulting colonies counted. Kill curve results averaged between three experiments, each with an average of three technical replicates. Error bars are ±one standard deviation of the averaged data. Results are depicted in FIG. 8. D376A, and its robust tolerance to IM, is surprising as this has not been described in cassava to date. W574L also has robust tolerance to both TP and IM, although growth is inconsistent.

Example 3: Production of Cassava Plant Tissues from Culture

In vitro plantlets are maintained by monthly subcultures as shoot cuttings following the procedure described by Hankoua et al., Regeneration of a wide range of African cassava genotypes via shoot organogenesis from cotyledon of maturing somatic embryos and conformity of the field-established regenerants. Plant Cell, Tiss. Org. 81(2):200-211, 2005. Shoot apical meristems and immature leaf lobes (0.1-0.9 mm in length) are exited from plantlets 10-14-days after previous subculture and cultured on picloram-based embryo induction medium (P-CIM) for the induction of primary somatic embryos and organized embryogenic structure (OES). OES are divided into small clusters of 5-10 embryos each and transferred into cassava embryo maturation media (CMML) (Table 1) as described by Hankoua et al. (2005) to enhance their development into green cotyledon stage embryos. Green cotyledon pieces (about 5 mm$^2$ each), obtained from 14-15 days old cotyledonary stage embryos using scalpel blades, are placed on P-CIM for the production of secondary somatic embryos. Secondary somatic embryo clusters induced from P-CIM are transferred to CMML for maturation. Green somatic cotyledon pieces obtained from 14-15 day-old secondary stage embryos are placed on P-CIM for induction of cyclic somatic embryogenesis. OES induced from all cassava genotypes are fragmented into small pieces of about 5 mm$^2$ each and sub cultured onto friable callus induction medium and maintenance medium (FEC-IM) for the induction of friable embryogenic callus (FEC) as described by Taylor et al., Development of friable embryogenic callus and embryogenic suspension systems in cassava (*Manihot esculenta* Crantz), Nature Biotechnol. 14(6):726-730, 1996. FEC-IM is modified by the inclusion of 25-mg/l-casein hydrolysate and 2 μM copper sulfate. Calli with the potential to develop into FECs and induced FECs are sub-cultured on the same medium for the selection and proliferation of high quality friable embryogenesis callus. Embryogenic suspensions are initiated by transferring approximately 35 mg of pure FEC into 50 ml embryogenesis suspension medium (EMS) and culturing as described by Taylor et al. (1996). All cultures are incubated in the growth room at temperatures varying from 25° C. to 28° C. either under total dark (one week) for embryo induction from leaf lobe and apical meristem explants or with a photoperiod of 16 h (40-100 μm photon s$^{-1}$ m$^{-2}$ PAR) for multiplication and maintenance of all other tissues. Unless otherwise stipulated, all culture media are supplemented with 0.6% agar.

Example 4. Isolation of Cassava Protoplasts

Two grams of FEC is placed in Petri dishes containing 10 ml of cell wall digestion solution. Cell wall digestion solution consisted of a mixture of cell wall degrading enzymes; 10 mg/l pectolyase, 10 g/l cellulose, 200 mg/l macero enzym growth regulators (NAA 1 mg/l, 2,4-D 1 mg/l, Zeatin 1 mg/l), major salts (368 mg/l CaCl$_2$; 34 mg/l KH$_2$PO$_4$; 740 mg/KNO$_3$; 492 mg/l MgSO$_4$.7H$_2$O); minor salts (19.2 mg/l NA-EDTA; 14 mg/l FeSO$_4$.7H$_2$O) and osmoticum (91 g/l D-mannitol) and 0.5 g/l MES. The cell wall degrading enzymes cellulase (1-10 g/l) plus Macerozyme (200 mg/l) are successful for protoplast isolation. The extra addition of Pectolyase (0.001-0.01 g/l) and/or Driselase (0.02 g/l) increased the yield of protoplasts. After 18 h of incubation, 10 ml of washing medium is added to the solution. Washing medium with an osmolarity 0.530 mOsm/ kg consisted of major salts (see cell wall digestion solution), 45.5 g/l mannitol and 7.3 g/l NaCl. The digested tissue is filtered through a 73 µM pore size filter (PA 55/34 Nybolt-Switzerland) into a 250 ml beaker glass. The filtrate is divided equally over two 12 ml conical screw cap tubes, and centrifuged at 600 rpm for 3 min. (Mistral 2000). The washing procedure is repeated once after removal of the supernatant. The protoplast solution is resuspended by floating on 9.5 ml solution containing major and minor salts (see cell wall digestion solution) and 105 g/l sucrose. The pH is 5.8 and the osmolarity 0.650 mOsm. The solution with protoplasts is allowed to equilibrate for 5 minutes before 0.5 ml of washing medium is gently added on the top. After centrifugation at 700 rpm for 15 min. (Mistral 2000), the protoplasts ware concentrated in a band between the sucrose and washing medium. The protoplast layer is harvested with a pasteur pipette and the yield is counted in a standard haemocytometer chamber.

Example 5: Protoplast Culture

Protoplasts ware cultured in media solidified with agarose 0.2% w/v in petri dishes containing 10 ml of the same liquid medium. The following media resulted in the formation of micro callus:

TM2G medium (Wolters et al., 1991) supplemented with only auxins (0.1-10 mg/l NAA or 0.1-10 mg/l Picloram, or 0.1-10 mg/l IAA, or 0.1-10 mg/l 2,4-D, or 0.1-10 mg/l Dicamba, or 0.1-10 mg/l, or 0.1-10 mg/l) or auxins plus cytokinins (0.01-1 mg/l zeatin, 0.01-1 mg/l 2-iP, 0.01-1 mg/l BA, 0.01-1 mg/l TDZ, 0.01-1 mg/l kinetin).

Medium A (Murashige and Skoog (1962) salts and vitamins, 4.5 g/l myo-inositol, 4.55 g/l mannitol, 3.8 g/l xylitol, 4.55 g/l sorbitol, 0.098 g/l MES, 40 mg/l adeninsulphate and 150 mg/l caseinhydrolysate, 0.5 mg/l d-calcium-panthotenate, 0.1 mg/l choline-chloride, 0.5 mg/l ascorbic acid, 2.5 mg/l nicotinic acid, 1 mg/l pyridoxine-HCl, 10 mg/l thiamine-HCl, 0.5 mg/l folic acid, 0.05 mg/l biotine, 0.5 mg/l glycine, 0.1 mg/l L-cysteine and 0.25 mg/l riboflavine and 59.40 g/l glucose) supplemented with only auxins (0.1-10 mg/l NAA or 0.1-10 mg/l Picloram, or 0.1-10 mg/l IAA, or 0.1-10 mg/l 2,4-D, or 0.1-10 mg/l Dicamba plus cytokinins (0.01-1 mg/l zeatin, 0.01-1 mg/l 2-iP, 0.01-1 mg/l BA, 0.01-1 mg/l TDZ, 0.01-1 mg/l kinetin).

The media are refreshed every 10 days, by replacing 9 ml with fresh medium. After two months of culture in the first medium, high quality FEC is selected and either culture for further proliferation or for maturation. For proliferation FEC is transferred to Gresshoff and Doy medium supplemented with 40 g/l sucrose, 7 g/l Daichin agar and 2 mg/l picloram (GD4). After 3 weeks the FEC is transferred to a Gresshoff and Doy medium supplemented with 20 g/l sucrose, 7 g/l agar and 10 mg/l Picloram (GD2). Suspension cultures ware initiated by transferring 1.0 g of FEC to liquid SH6% medium supplemented with 10 mg/l Picloram. Two weeks later the suspension is divided over new flasks with an initial packed cell volume of 1.0 nil.

After 2 months of culture, $10^4$ protoplasts cultured in TM2G supplemented with 0.5 mg/l NAA and 1 mg/l Zeatin at a density of $10^5$/ml can produce>1000 micro-calli, whereas $10^4$ protoplasts cultured at a density of $10^6$/ml can produced 64 micro-calli. Replacing TM2G medium with medium A reduced at both densities the number of micro-calli significantly. At this stage at least three types of calli can be distinguished. One type consists of globular shaped embryos which are mostly observed in protoplasts cultured at a density of $10^6$. Some of them develop cotyledon like structures, light green in color. However, these embryos may not germinate properly. Another type is fast growing and consisted of a large compact callus. This callus never develops embryos. The third type is highly friable callus and is observed at both densities. At a density of $2-5\times10^5$ (medium TM2G) about 60% of the calli are friable and embryogenic. The FEC can either be subcultured for further proliferation or for maturation.

Example 6: Proliferation of FEC Derived from Protoplasts

Following selection of FEC, 0.1 g of it cultured for three weeks on GD4 plus 2 mg/l Picloram increases into 0.7 g of tissue. More than 95% of the tissue consists of high quality FEC. Subsequently, this tissue is maintained by subcultures of three weeks on GD2 medium supplemented with 10 mg/l Picloram. To initiate suspension cultures, FEC is transferred to liquid medium.

Example 7: Maturation of FEC Derived from Protoplasts

FEC isolated after two months of culture in TM2G is cultured on maturation medium. Maturation medium consisted of Murashige and Skoog (1962) salts and vitamins, 10 g/l Daichin agar, 0.1 g/l myo-inositol, 20 g/l sucrose, 18.2 g/l mannitol, 0.48 g/l MES, 0.1 g/l caseinhydrolysate, 0.08 g/l adenine sulphate, 0.5 mg/l d-calcium-panthotenate, 0.1 mg/l choline chloride, 0.5 mg/l ascorbic acid, 2. Mg/l nicotinic acid, 1 mg/l pyridoxine-HCl, 10 mg/l thiamine HCl, 0.5 mg/l folic acid, 0.05 mg/l biotin, 0.5 mg/l glycine, 0.1 mg/l L-cysteine, 0.25 mg/l riboflavine and 1 mg/l picloram. This maturation medium is refreshed every 3 weeks.

On this medium there is a gradual shift from proliferation to maturation. As a result the packed cell volume increases by a factor 4 after two weeks of culture in liquid maturation medium. Also after transfer to solid maturation medium there is proliferation. After two weeks on solid medium most of the embryos reach a globular shape and only a few of these globular embryos developed further. The first torpedo shaped embryos become visible after one month of culture on solid maturation medium. The number of mature and torpedo shaped embryos are not correlated with the plating efficiency but with the density of the initially cultured protoplasts. No such embryos are obtained if protoplasts are cultured on TM2G without growth regulators. The highest number of mature and torpedo shaped embryos is formed from protoplasts cultured on TM2G supplemented with 0.5 mg/l NAA and 1 mg/l Zeatin. After 3 months of culture between 60 and 200 torpedo shaped and mature embryos are isolated per agarose drop. Torpedo shaped embryos become mature at high frequency if they are cultured on fresh maturation medium or on MS2 plus 0.1 mg/l BAP.

Example 8: Secondary Somatic Embryogenesis and Germination of Mature Embryos Derived from Protoplasts In both liquid and solid medium 2,4-D is superior for induction of secondary embryogenesis as compared to NAA. If mature embryos are first cultured in 2,4-D and then in liquid NAA the response is comparable with culture in 2,4-D alone. Also embryos which first had undergone a cycle of secondary somatic embryogenesis in medium with 2,4-D, produced highly efficient secondary embryos in MS20 supplemented with 10 mg/l NAA. Desiccation stimulated normal germination of NAA induced embryos. However, the desiccated embryos, require a medium supplemented with cytokinins such as benzytaminopurine (BAP) for high frequency germination. With 1 mg/l BAP plants with thick and short taproots and branched shoots with short internodes are formed. With 0.1 mg/l BAP the taproots are thin and slender. Also desiccated embryos which are cultured in the dark require a lower concentration of BAP and, furthermore, these embryos germinate faster than embryos cultured in the light. Complete plants are obtained four weeks after the start of somatic embryo induction. 2,4-D induced embryos show a different response. In all genotypes desiccation stimulates root formation. Embryos cultured in the dark form predominantly adventitious roots, whereas embryos cultured in the light form predominantly taproots.

Example 9: CRISPRs and GRONs in Cassava

This example demonstrates AHAS W574S conversion in *Manihot esculenta* at 4 weeks after PEG delivery of CRISPR-Cas9 plasmids and GRONs into protoplasts. The CRISPR-Cas9 used in this experiment targets the AHAS genes in the cassava genome by introducing into protoplasts plasmid(s) encoding the Cas9 gene and sgRNAs. The sgRNA is a fusion of CRISPR RNA (crRNA) and trans-activating crRNA (tracrRNA). The crRNA guides the Cas9 to the target genes, where Cas9 creates a double-stranded break in the AHAS genes and the GRONs are used as a template to convert the AHAS genes in a site-directed manner.

Methods

Figure 9A:
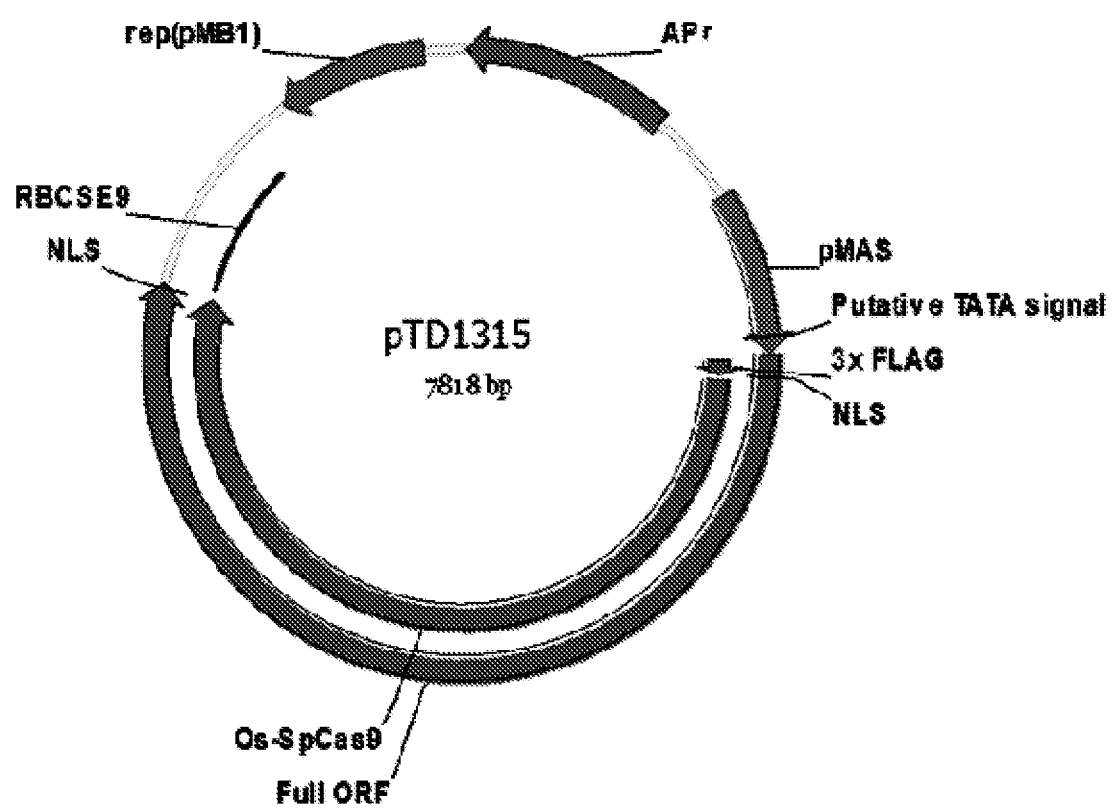
FIG. 9A shows the structure of plasmid pTD1315.
Figure 9B:
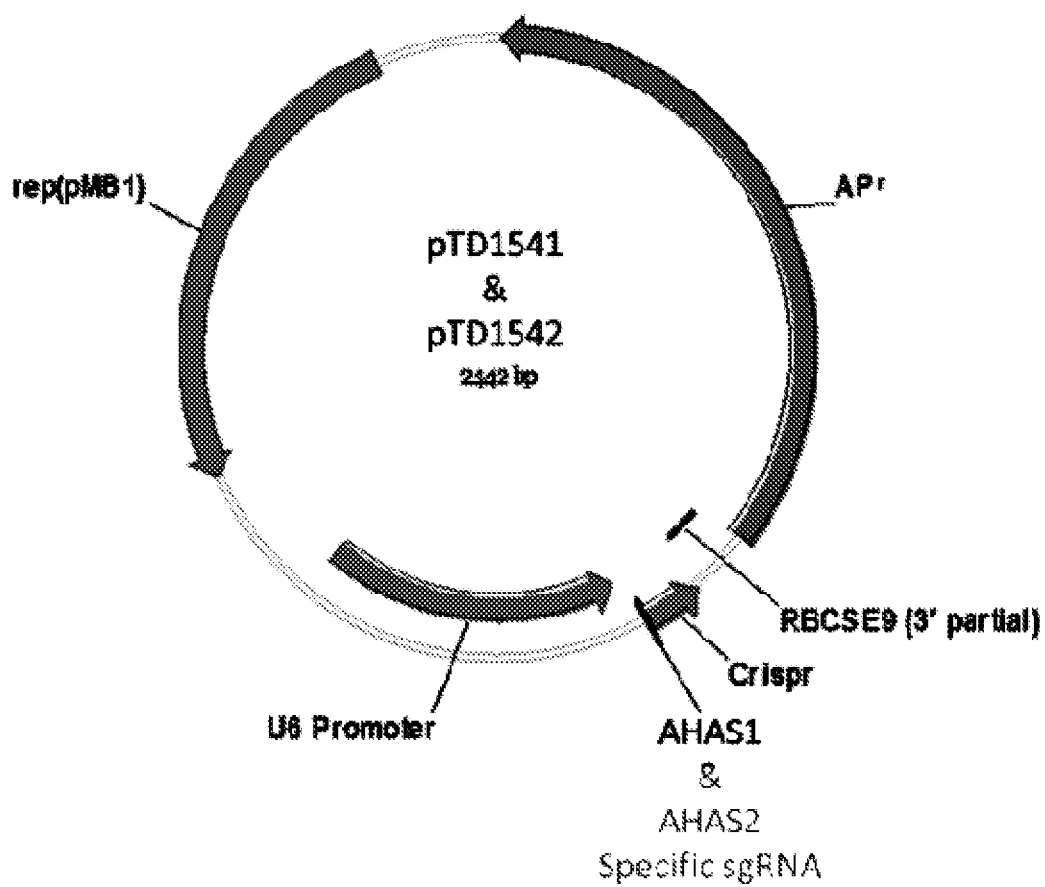
FIG. 9B shows the structure of plasmids pTD1541 and pTD1542.

Cassava protoplasts were isolated from root cell suspensions. The CRISPR-Cas9 encoding plasmid (pTD1315, FIG. 9A) contains the MAS promoter driving the Cas9 coding sequence with an rbcSE9 terminator. Separate sgRNA plasmids (pTD1541 and pTD1542, FIG. 9B) were used with the rice U6 promoter promoter driving the sgRNAs with a rbcSE9 terminator. The plasmids were introduced into protoplasts by PEG mediated delivery at a final concentration of 0.08 µg/µl. GRONs (AHAS1-2-C and AHAS2-2-C, see below) were used at a final concentration of 0.5 µM. Protoplasts were cultured in liquid medium, and incubated in the dark at 28° C. for two weeks after which they were moved to a 50 rpm rotary shaker at 28° C. in indirect low light. Individual samples of 30 k microcalli were analyzed by NGS 4 weeks after CRISPR-Cas9 plasmids and/or GRON delivery, to determine the percentage of cells (DNA reads) carrying the AHAS conversion and having indels in the AHAS gene.

The CRISPR consists of two components: the plant codon-optimized *Streptococcus pyogenes* Cas9 (SpCas9) and sgRNA both of which were expressed from the same plasmid. The sgRNA is a fusion of CRISPR RNA (crRNA) and trans-activating crRNA (tracrRNA). The crRNA region contains the spacer sequence 5'-ACGAGGAGGGCT-TGGGTTGTGG-3 (SEQ ID NO: 6) used to guide the Cas9 nuclease to the target gene. In this experiment the CRISPRs target the AHAS genes. The following sequences were utilized in these methods:

```
AHAS1 sgRNA (SEQ ID NO: 7):
ATTTGGGAATGGTGGTACAATGGGAGG

AHAS2 sgRNA (SEQ ID NO: 8):
GAACAATCAACATCTGGGTATGGTTGTTCAATGG

AHAS1-2-C GRON (SEQ ID NO: 9):
TCTGCCAATTAAAATAATGCTTTTGAATAATCAGCATTTGGGAATGGTGG

TACAATCGGAAGACCGATTCTACAAGGCTAATAGAGCTCATACTTATTTG

GGGGATCCATCAA

AHAS2-2-C GRON (SEQ ID NO: 10):
ACCTGCCTGTGAAGATCTTGTTACTGAACAATCAACATCTGGGTATGGTT

GTTCAGTCGGAGGACAGATTCTATCATTCCAACAGAGCACATACATATTT

AGGGAACCCATCA
```

Results

At 4 weeks, rice protoplasts have 0.024% AHAS1 and 0.007% AHAS2 gene conversion as determined by NGS. GRON only controls with no CRISPR-Cas9 and the untreated controls showed no conversion. Additionally, these data show that the CRISPR-Cas9 is active and able to cleave the AHAS target genes and form indels at a rate up to 52.1%.

REFERENCES

Datta S K, Datta K, Soltanifar N, Donn G, Potrykus I (1992) Herbicide-resistant Indica rice plants from IRRI breeding line IR72 after PEG-mediated transformation of protoplasts. Plant Molec. Biol. 20:619-629

Dovzhenko A (2001) Towards plastid transformation in rapeseed (*Brassica napus* L.) and sugarbeet (*Beta vulgaris* L.). PhD Dissertation, LMU Munich, Faculty of Biology Duggleby, R. G. McCourt, J. A.; Guddat L. W. Plant Physiology and Biochemistry. 46, (2008) 309-324.

Edwards K, Johnstone C, Thompson C (1991) A simple and rapid method for the preparation of plant genomic DNA for PCR analysis. Nucleic Acids Res. 19:1349.

Frigerio L, Vitale A, Lord J M, Ceriotti A, Roberts L M (1998) Free ricin A chain, proricin, and native toxin have different cellular fates when expressed in tobacco protoplasts. J Biol Chem 273:14194-14199

Fang L Y, Gross P R, Chen C H, Lillis M (1992) Sequence of two acetohydroxyacid synthase genes from *Zea mays*. Plant Mol Biol. 18(6):1185-7

Gharti-Chhetri G B, Cherdshewasart W, Dewulf J, Jacobs M, Negrutiu I (1992) Polyethylene glycol-mediated direct gene transfer in *Nicotiana* spp. Physiol. Plant. 85:345-351

Klaus S (2003) Markerfreie transplastome Tabakpflanzen (Marker-free transplastomic tobacco plants). PhD Dissertation, LMU Munich, Faculty of Biology Miki B, Huang B, Bird S, Kemble R, Simmonds D, Keller W (1989) A procedure for the microinjection of plant cells and protoplasts. Meth. Cell Science 12:139-144

Pelletier G, Primard C, Vedel F, Chetrit P, Remy R, Rouselle P, Renard M (1983) Intergeneric cytoplasm hybridization in Cruciferae by protoplast fusion. Mol. Gen. Genet. 191: 244-250

Schnorf M, Neuhaus-Url G, Galli A, Iida S, Potrykus I, Neuhaus G (1991) An improved approach for transformation of plant cells by microinjection: molecular and genetic analysis. Transgen. Res. 1:23-30

Tan S, Evans R R, Dahmer M L, Singh B K, Shaner D L (2005) Imidazolinone-tolerant crops: history, current status and future. Pest Manag Sci. 61(3):246-57.

Unless otherwise defined, all technical and scientific terms used herein have the same meaning as commonly understood by one of ordinary skill in the art to which this invention belongs.

The inventions illustratively described herein may suitably be practiced in the absence of any element or elements, limitation or limitations, not specifically disclosed herein. Thus, for example, the terms "comprising," "including," "containing," etc. shall be read expansively and without limitation. Additionally, the terms and expressions employed herein have been used as terms of description and not of limitation, and there is no intention in the use of such terms and expressions of excluding any equivalents of the features shown and described or portions thereof. It is recognized that various modifications are possible within the scope of the invention claimed.

Thus, it should be understood that although the present invention has been specifically disclosed by preferred embodiments and optional features, modification, improvement, and variation of the inventions disclosed may be resorted to by those skilled in the art, and that such modifications, improvements and variations are considered to be within the scope of this invention. The materials, methods, and examples provided here are representative of preferred embodiments, are exemplary, and are not intended as limitations on the scope of the invention.

The invention has been described broadly and generically herein. Each of the narrower species and subgeneric groupings falling within the generic disclosure also form part of the invention. This includes the generic description of the invention with a proviso or negative limitation removing any subject matter from the genus, regardless of whether or not the excised material is specifically recited herein.

In addition, where features or aspects of the invention are described in terms of Markush groups, those skilled in the art will recognize that the invention is also thereby described in terms of any individual member or subgroup of members of the Markush group.

All publications, patent applications, patents, and other references mentioned herein are expressly incorporated by reference in their entirety, to the same extent as if each were incorporated by reference individually. In case of conflict, the present specification, including definitions, will control.

Other embodiments are set forth within the following claims.

What is claimed is:

1. An isolated nucleic acid encoding a Cassava acetohydroxyacid synthase (AHAS) protein comprising a tryptophan to serine mutation at position 562 of SEQ ID NO: 1.

2. An expression vector comprising a nucleic acid encoding a Cassava acetohydroxyacid synthase (AHAS) protein comprising a mutation at one or more amino acid positions, one of which corresponds to a tryptophan to serine mutation at position 562 of SEQ ID NO: 1.

3. A plant, or a plant seed, comprising a Cassava acetohydroxyacid synthase (AHAS) gene, wherein said gene encodes a Cassava acetohydroxyacid synthase (AHAS) protein comprising a tryptophan to serine mutation at position 562 of SEQ ID NO: 1.

4. The plant or plant seed of claim 3, wherein said plant is resistant to inhibition by an AHAS-inhibiting herbicide, wherein said AHAS-inhibiting herbicide is optionally selected from the group consisting of herbicides of: imidazolinone, sulfonylurea, triazolopyrimidine, pyrimidinylthiobenzoate, sulfonylamino-carbonyltriazolinone, and mixtures thereof.

5. The plant or plant seed of claim 3, wherein said plant is resistant to inhibition by each of an imidazolinone herbicide and a triazolopyrimidine herbicide.

6. A plant comprising a nucleic acid encoding a Cassava acetohydroxyacid synthase (AHAS) protein comprising a tryptophan to serine mutation at position 562 of SEQ ID NO: 1, wherein said plant is resistant to inhibition by each of an imidazolinone herbicide and a triazolopyrimidine herbicide, or a seed obtained therefrom.

7. A method for producing an herbicide-resistant Cassava plant, said method comprising:
   introducing into a Cassava plant cell a gene repair oligonucleobase (GRON) with a targeted mutation in an acetohydroxyacid synthase (AHAS) gene to produce a Cassava plant cell with a Cassava AHAS gene that expresses a protein comprising a mutation at one or more amino acid positions, one of which corresponds to a tryptophan to serine mutation at position 562 of SEQ ID NO: 1;
   identifying a Cassava plant cell having substantially normal growth and catalytic activity as compared to a corresponding wild-type plant cell in the presence of an AHAS-inhibiting herbicide; and
   regenerating a non-transgenic herbicide-resistant plant having a mutated Cassava AHAS gene from said plant cell.

8. A method for increasing the herbicide-resistance of a Cassava plant comprising crossing a first Cassava plant to a second Cassava plant, wherein said first plant comprises a Cassava acetohydroxyacid synthase (AHAS) gene, wherein said gene encodes a Cassava acetohydroxyacid synthase (AHAS) protein comprising a mutation at one or more amino acid positions, one of which corresponds to a tryptophan to serine mutation at position 562 of SEQ ID NO: 1; screening a population resulting from the cross for increased AHAS herbicide-resistance; selecting a member resulting from the cross having increased AHAS herbicide-resistance; and producing seeds resulting from the cross.

9. An isolated nucleic acid encoding a Cassava acetohydroxyacid synthase (AHAS) protein comprising an aspartic acid to alanine mutation at position 364 of SEQ ID NO: 1.

10. An expression vector comprising a nucleic acid encoding a Euphorbiaceae acetohydroxyacid synthase (AHAS) protein comprising a mutation at one or more amino acid positions, one of which corresponds to an aspartic acid to alanine mutation at position 364 of SEQ ID NO: 1.

11. A plant, or a plant seed, comprising a Cassava acetohydroxyacid synthase (AHAS) gene, wherein said gene encodes a Cassava acetohydroxyacid synthase (AHAS) protein comprising an aspartic acid to alanine mutation at position 364 of SEQ ID NO: 1.

12. The plant or plant seed of claim 11, wherein said plant is resistant to inhibition by an AHAS-inhibiting herbicide, wherein said AHAS-inhibiting herbicide is optionally selected from the group consisting of herbicides of: imidazolinone, sulfonylurea, triazolopyrimidine, pyrimidinylthiobenzoate, sulfonylamino-carbonyltriazolinone, and mixtures thereof.

13. The plant or plant seed of claim 11, wherein said plant is resistant to inhibition by each of an imidazolinone herbicide and a triazolopyrimidine herbicide.

14. A method for producing an herbicide-resistant Cassava plant, said method comprising:
   introducing into a Cassava plant cell a gene repair oligonucleobase (GRON) with a targeted mutation in an acetohydroxyacid synthase (AHAS) gene to produce a Cassava plant cell with a Cassava AHAS gene that expresses a protein comprising a mutation at one or more amino acid positions, one of which corresponds to an aspartic acid to alanine mutation at position 364 of SEQ ID NO: 1;
   identifying a Cassava plant cell having substantially normal growth and catalytic activity as compared to a corresponding wild-type plant cell in the presence of an AHAS-inhibiting herbicide; and
   regenerating a non-transgenic herbicide-resistant plant having a mutated Cassava AHAS gene from said plant cell.

15. A method for increasing the herbicide-resistance of a Cassava plant comprising crossing a first Cassava plant to a second Cassava plant, wherein said first plant comprises a Cassava acetohydroxyacid synthase (AHAS) gene, wherein said gene encodes a Cassava acetohydroxyacid synthase (AHAS) protein comprising a mutation at one or more amino acid positions, one of which corresponds to an aspartic acid to alanine mutation at position 364 of SEQ ID NO: 1; screening a population resulting from the cross for increased AHAS herbicide-resistance; selecting a member resulting from the cross having increased AHAS herbicide-resistance; and producing seeds resulting from the cross.

* * * * *

SEQUENCE LISTING

```
<160> NUMBER OF SEQ ID NOS: 10

<210> SEQ ID NO 1
<211> LENGTH: 658
<212> TYPE: PRT
<213> ORGANISM: Manihot esculenta
<220> FEATURE:
<221> NAME/KEY: misc_feature
<223> OTHER INFORMATION: Amino acid sequence for a wild type Cassava
      (Manihot esculenta) AHAS protein

<400> SEQUENCE: 1

Met Ala Ala Ala Ser Thr Ser Ala Ala Thr Thr Ile Pro Lys Pro Ser
 1               5                  10                  15

Ser His Ile Ser Ser Ser Ser Arg Ser Ser Ile Phe Ile Ser Arg Phe
            20                  25                  30

Thr Leu Pro Leu Ser Leu Asn Pro Gln Lys Ala Ile Pro His Arg Ser
        35                  40                  45

Leu His Ile Ser Asn Ser Val Ser Lys Pro Thr Thr Pro Ala Pro Ser
    50                  55                  60

Ser Ser Thr Thr Leu Thr Ile Pro Gln Ala Ser Pro Pro Arg Phe Ser
65                  70                  75                  80

Pro Asp Glu Ala Arg Lys Gly Ala Asp Ile Leu Val Glu Ala Leu Glu
                85                  90                  95

Arg Gln Gly Val Thr Asp Val Phe Ala Tyr Pro Gly Gly Ala Ser Met
            100                 105                 110

Glu Ile His Gln Ala Leu Thr Arg Ser Pro Ile Ile Arg Asn Val Leu
        115                 120                 125

Pro Arg His Glu Gln Gly Gly Val Phe Ala Ala Glu Gly Tyr Ala Arg
    130                 135                 140

Ala Ser Gly Lys Pro Gly Val Cys Ile Ala Thr Ser Gly Pro Gly Ala
145                 150                 155                 160

Thr Asn Leu Val Ser Gly Leu Ala Asp Ala Leu Leu Asp Ser Val Pro
                165                 170                 175

Ile Val Ala Ile Thr Gly Gln Val Pro Arg Arg Met Ile Gly Thr Asp
            180                 185                 190

Ala Phe Gln Glu Thr Pro Ile Val Glu Val Thr Arg Ser Ile Thr Lys
        195                 200                 205
```

-continued

His Asn Tyr Leu Val Leu Asp Val Asp Asp Ile Pro Arg Ile Val Ser
    210             215                 220

Glu Ala Phe Phe Leu Ala Thr Ser Gly Arg Pro Gly Pro Val Leu Ile
225             230                 235                 240

Asp Val Pro Lys Asp Ile Gln Gln Leu Ala Val Pro Asn Trp Asn
                245             250                 255

Thr Pro Ile Lys Leu Pro Gly Tyr Met Ser Arg Leu Pro Lys Val Pro
            260             265                 270

Asn Glu Ser His Leu Glu Gln Ile Val Arg Leu Ile Phe Glu Ser Lys
        275             280                 285

Lys Pro Val Leu Tyr Val Gly Gly Cys Leu Asn Ser Ser Glu Glu
290             295                 300

Leu Arg Lys Phe Val Glu Leu Thr Gly Ile Pro Val Ala Ser Thr Leu
305             310                 315                 320

Met Gly Leu Gly Ala Phe Pro Val Gly His Glu Leu Ser Leu Gln Met
                325             330                 335

Leu Gly Met His Gly Thr Val Tyr Ala Asn Tyr Ser Val Asp Lys Ser
            340             345                 350

Asp Leu Leu Leu Ala Phe Gly Val Arg Phe Asp Asp Arg Val Thr Gly
                355             360                 365

Lys Leu Glu Ala Phe Ala Ser Arg Ala Lys Ile Val His Ile Asp Ile
370             375                 380

Asp Ser Ala Glu Ile Gly Lys Asn Lys Gln Pro His Val Ser Val Cys
385             390                 395                 400

Ala Asp Val Lys Phe Ala Leu Gln Gly Met Asn Lys Ile Leu Glu Ser
                405             410                 415

Arg Cys Ala Lys Ser Lys Leu Asp Phe Lys Ala Trp Arg Glu Glu Leu
            420             425                 430

Asn Glu Gln Lys Ser Lys Tyr Pro Leu Lys Tyr Lys Thr Phe Gly Asp
            435             440                 445

Ala Ile Pro Pro Gln Tyr Ala Ile Gln Val Leu Asp Glu Leu Thr Asp
450             455                 460

Gly Asn Ala Ile Ile Ser Thr Gly Val Gly Gln His Gln Met Trp Ala
465             470                 475                 480

Ala Gln Phe Tyr Lys Tyr Lys Arg Pro Arg Gln Trp Leu Thr Ser Gly
                485             490                 495

Gly Leu Gly Ala Met Gly Phe Gly Leu Pro Ala Ala Ile Gly Ala Ala
            500             505                 510

Val Ala Asn Pro Gly Ala Val Val Asp Ile Asp Gly Asp Gly Ser
            515             520                 525

Phe Ile Met Asn Val Gln Glu Leu Ala Thr Ile Arg Val Glu Asn Leu
530             535                 540

Pro Ile Lys Ile Met Leu Leu Asn Asn Gln His Leu Gly Met Val Val
545             550                 555                 560

Gln Trp Glu Asp Arg Phe Tyr Lys Ala Asn Arg Ala His Thr Tyr Leu
                565             570                 575

Gly Asp Pro Ser Lys Glu Ser Glu Ile Phe Pro Asn Met Leu Lys Phe
            580             585                 590

Ala Glu Ala Cys Gly Ile Pro Ala Ala Arg Val Thr Arg Lys Glu Gly
            595             600                 605

Leu Arg Met Ala Ile Gln Lys Met Leu Asp Thr Pro Gly Pro Tyr Leu
610             615                 620

Leu Asp Val Ile Val Pro His Gln Glu His Val Leu Pro Met Ile Pro
625                 630                 635                 640

Ser Gly Gly Ala Phe Lys Asp Val Ile Thr Glu Gly Asp Gly Arg Thr
                645                 650                 655

Lys Tyr

<210> SEQ ID NO 2
<211> LENGTH: 1977
<212> TYPE: DNA
<213> ORGANISM: Manihot esculenta
<220> FEATURE:
<221> NAME/KEY: misc_feature
<223> OTHER INFORMATION: Nucleotide sequence encoding a wild type
      Cassava (Manihot esculenta) AHAS protein

<400> SEQUENCE: 2

| | |
|---|---|
| atggcggcgg cgtctaccte tgcggctacc actatcccta aaccctcttc tcacatttct | 60 |
| tcctcctcca gatcttcaat cttcatttcc agattcaccc tcccattgtc tctcaacccc | 120 |
| caaaaggcca ttcctcaccg ctctctccac atatcaaact ctgtctctaa acctacaacc | 180 |
| cctgccccct catcctccac caccttaacc attcctcaag cgtctcctcc caggtttttct | 240 |
| cctgatgaag ctcgaaaagg cgccgacatc ctcgttgaag cgctggaacg ccaagggggtc | 300 |
| actgatgtat ttgcttatcc aggcggcgca tccatggaga tccatcaagc cctgactcgc | 360 |
| tcacctataa ttcgcaatgt cctcccgcgc catgagcaag tgggggtctt tgcggctgag | 420 |
| ggatatgctc gcgcttctgg caagcctggc gtctgtatcg caacctcggg accccggcgct | 480 |
| acaaatctcg taagtggctt ggcagacgct ctccttgaca gcgtccccat tgtggctatc | 540 |
| accggccaag ttcctcgccg catgattggc accgacgcat tccaagaaac tcccattgtt | 600 |
| gaggtaactc ggtcaataac taagcacaat tacctggtcc ttgatgttga tgatattcct | 660 |
| agaattgtaa gtgaagcttt cttttttggcc acctcgggac gtcctggccc agttctgatt | 720 |
| gatgtaccaa aagatataca acaacaatta gctgttccaa attggaatac acctattaaa | 780 |
| ttgcctggtt acatgtcgag gttgcctaaa gtgcccaacg aatcacattt ggagcagatt | 840 |
| gtgaggctaa tttttgagtc aaagaaaccg gttttatacg tgggaggtgg gtgttttaaat | 900 |
| tcaagtgagg agttgagaaa gtttgtcgag ttaactggga tcccagtggc tagtactttg | 960 |
| atggggctcg gagcattccc agttggccac gaattgtcat acaaaatgct tggaatgcat | 1020 |
| ggaactgttt atgctaacta ctcggtggat aagagtgatt tgttgcttgc gtttgggggtg | 1080 |
| aggtttgatg acagggtgac aggcaagctt gaggcctttg caagcagagc taagattgtt | 1140 |
| cacattgata ttgattccgc tgagattggg aaaaataagc agccccatgt gtctgttttgt | 1200 |
| gcagatgtga gtttgccctt gcaagggatg aacaagattt tggagagcag atgtgctaag | 1260 |
| agtaagctag attttaaggc ttggagggag gagttgaatg agcagaaaag taaatatcca | 1320 |
| ttgaaataca agacatttgg agatgcaatt cctcctcagt acgccataca agttctcgat | 1380 |
| gaattaacag atgggaatgc cattataagt actggcgttg acaacatca gatgtgggct | 1440 |
| gctcaatttt acaagtacaa gagaccacgg caatggttga cgtcaggggg attaggggct | 1500 |
| atgggttttg gattgcctgc cgccattggg gctgctgttg ctaatcctgg tgcagttgtt | 1560 |
| gtagatattg atggtgatgg aagttttatc atgaatgtcc aggagttggc aacaattcgt | 1620 |
| gtggagaatc tgccaattaa aataatgctt ttgaataatc agcatttggg aatggtggta | 1680 |
| caatgggagg accgattcta caaggctaat agagctcata cttatttggg ggatccatca | 1740 |
| aaggagtctg agatttttccc caatatgttg aagtttgcag aagcttgtgg aatacctgct | 1800 |

```
gctcgcgtga caagaaaaga gggtcttaga atggcgattc agaaaatgct agatactcca    1860
gggccatact tgttggatgt gattgtgccc catcaagaac atgtgctgcc catgatccca    1920
agtgggggag cttttaagga tgtgataact gagggtgatg aagaacgaa gtattga        1977

<210> SEQ ID NO 3
<211> LENGTH: 658
<212> TYPE: PRT
<213> ORGANISM: Manihot esculenta
<220> FEATURE:
<221> NAME/KEY: misc_feature
<223> OTHER INFORMATION: Cassava (Manihot esculenta) AHAS comprising a
      W574S mutation

<400> SEQUENCE: 3
```

| | | | | | | | | | | | | | | |
|---|---|---|---|---|---|---|---|---|---|---|---|---|---|---|
| Met | Ala | Ala | Ala | Ser | Thr | Ser | Ala | Ala | Thr | Thr | Ile | Pro | Lys | Pro | Ser |
| 1 | | | | 5 | | | | | 10 | | | | | 15 | |

```
Met Ala Ala Ala Ser Thr Ser Ala Ala Thr Thr Ile Pro Lys Pro Ser
1               5                   10                  15

Ser His Ile Ser Ser Ser Arg Ser Ile Phe Ile Ser Arg Phe
            20                  25                  30

Thr Leu Pro Leu Ser Leu Asn Pro Gln Lys Ala Ile Pro His Arg Ser
            35                  40                  45

Leu His Ile Ser Asn Ser Val Ser Lys Pro Thr Thr Pro Ala Pro Ser
        50                  55                  60

Ser Ser Thr Thr Leu Thr Ile Pro Gln Ala Ser Pro Pro Arg Phe Ser
65                  70                  75                  80

Pro Asp Glu Ala Arg Lys Gly Ala Asp Ile Leu Val Glu Ala Leu Glu
                85                  90                  95

Arg Gln Gly Val Thr Asp Val Phe Ala Tyr Pro Gly Gly Ala Ser Met
            100                 105                 110

Glu Ile His Gln Ala Leu Thr Arg Ser Pro Ile Ile Arg Asn Val Leu
        115                 120                 125

Pro Arg His Glu Gln Gly Gly Val Phe Ala Ala Glu Gly Tyr Ala Arg
    130                 135                 140

Ala Ser Gly Lys Pro Gly Val Cys Ile Ala Thr Ser Gly Pro Gly Ala
145                 150                 155                 160

Thr Asn Leu Val Ser Gly Leu Ala Asp Ala Leu Leu Asp Ser Val Pro
                165                 170                 175

Ile Val Ala Ile Thr Gly Gln Val Pro Arg Arg Met Ile Gly Thr Asp
            180                 185                 190

Ala Phe Gln Glu Thr Pro Ile Val Glu Val Thr Arg Ser Ile Thr Lys
        195                 200                 205

His Asn Tyr Leu Val Leu Asp Val Asp Asp Ile Pro Arg Ile Val Ser
    210                 215                 220

Glu Ala Phe Phe Leu Ala Thr Ser Gly Arg Pro Gly Pro Val Leu Ile
225                 230                 235                 240

Asp Val Pro Lys Asp Ile Gln Gln Gln Leu Ala Val Pro Asn Trp Asn
                245                 250                 255

Thr Pro Ile Lys Leu Pro Gly Tyr Met Ser Arg Leu Pro Lys Val Pro
            260                 265                 270

Asn Glu Ser His Leu Glu Gln Ile Val Arg Leu Ile Phe Glu Ser Lys
        275                 280                 285

Lys Pro Val Leu Tyr Val Gly Gly Gly Cys Leu Asn Ser Ser Glu Glu
    290                 295                 300
```

```
Leu Arg Lys Phe Val Glu Leu Thr Gly Ile Pro Val Ala Ser Thr Leu
305                 310                 315                 320

Met Gly Leu Gly Ala Phe Pro Val Gly His Glu Leu Ser Leu Gln Met
            325                 330                 335

Leu Gly Met His Gly Thr Val Tyr Ala Asn Tyr Ser Val Asp Lys Ser
                340                 345                 350

Asp Leu Leu Leu Ala Phe Gly Val Arg Phe Asp Asp Arg Val Thr Gly
            355                 360                 365

Lys Leu Glu Ala Phe Ala Ser Arg Ala Lys Ile Val His Ile Asp Ile
    370                 375                 380

Asp Ser Ala Glu Ile Gly Lys Asn Lys Gln Pro His Val Ser Val Cys
385                 390                 395                 400

Ala Asp Val Lys Phe Ala Leu Gln Gly Met Asn Lys Ile Leu Glu Ser
                405                 410                 415

Arg Cys Ala Lys Ser Lys Leu Asp Phe Lys Ala Trp Arg Glu Glu Leu
            420                 425                 430

Asn Glu Gln Lys Ser Lys Tyr Pro Leu Lys Tyr Lys Thr Phe Gly Asp
    435                 440                 445

Ala Ile Pro Pro Gln Tyr Ala Ile Gln Val Leu Asp Glu Leu Thr Asp
450                 455                 460

Gly Asn Ala Ile Ile Ser Thr Gly Val Gly Gln His Gln Met Trp Ala
465                 470                 475                 480

Ala Gln Phe Tyr Lys Tyr Arg Pro Arg Gln Trp Leu Thr Ser Gly
                485                 490                 495

Gly Leu Gly Ala Met Gly Phe Gly Leu Pro Ala Ala Ile Gly Ala Ala
            500                 505                 510

Val Ala Asn Pro Gly Ala Val Val Asp Ile Asp Gly Asp Gly Ser
            515                 520                 525

Phe Ile Met Asn Val Gln Glu Leu Ala Thr Ile Arg Val Glu Asn Leu
530                 535                 540

Pro Ile Lys Ile Met Leu Leu Asn Asn Gln His Leu Gly Met Val Val
545                 550                 555                 560

Gln Ser Glu Asp Arg Phe Tyr Lys Ala Asn Arg Ala His Thr Tyr Leu
                565                 570                 575

Gly Asp Pro Ser Lys Glu Ser Glu Ile Phe Pro Asn Met Leu Lys Phe
            580                 585                 590

Ala Glu Ala Cys Gly Ile Pro Ala Ala Arg Val Thr Arg Lys Glu Gly
    595                 600                 605

Leu Arg Met Ala Ile Gln Lys Met Leu Asp Thr Pro Gly Pro Tyr Leu
610                 615                 620

Leu Asp Val Ile Val Pro His Gln Glu His Val Leu Pro Met Ile Pro
625                 630                 635                 640

Ser Gly Gly Ala Phe Lys Asp Val Ile Thr Glu Gly Asp Gly Arg Thr
                645                 650                 655

Lys Tyr

<210> SEQ ID NO 4
<211> LENGTH: 670
<212> TYPE: PRT
<213> ORGANISM: Arabidopsis thaliana
<220> FEATURE:
<221> NAME/KEY: misc_feature
<223> OTHER INFORMATION: Amino acid sequence for Arabidopsis AHAS I
```

```
<400> SEQUENCE: 4

Met Ala Ala Ala Thr Thr Thr Thr Thr Ser Ser Ser Ile Ser Phe
1               5                   10                  15

Ser Thr Lys Pro Ser Pro Ser Ser Lys Ser Pro Leu Pro Ile Ser
            20                  25                  30

Arg Phe Ser Leu Pro Phe Ser Leu Asn Pro Asn Lys Ser Ser Ser
        35                  40                  45

Ser Arg Arg Arg Gly Ile Lys Ser Ser Ser Pro Ser Ser Ile Ser Ala
50                      55                  60

Val Leu Asn Thr Thr Thr Asn Val Thr Thr Thr Pro Ser Pro Thr Lys
65                  70                  75                  80

Pro Thr Lys Pro Glu Thr Phe Ile Ser Arg Phe Ala Pro Asp Gln Pro
                85                  90                  95

Arg Lys Gly Ala Asp Ile Leu Val Glu Ala Leu Glu Arg Gln Gly Val
            100                 105                 110

Glu Thr Val Phe Ala Tyr Pro Gly Gly Ala Ser Met Glu Ile His Gln
            115                 120                 125

Ala Leu Thr Arg Ser Ser Ile Arg Asn Val Leu Pro Arg His Glu
130                 135                 140

Gln Gly Gly Val Phe Ala Ala Glu Gly Tyr Ala Arg Ser Ser Gly Lys
145                 150                 155                 160

Pro Gly Ile Cys Ile Ala Thr Ser Gly Pro Gly Ala Thr Asn Leu Val
                165                 170                 175

Ser Gly Leu Ala Asp Ala Leu Leu Asp Ser Val Pro Leu Val Ala Ile
            180                 185                 190

Thr Gly Gln Val Pro Arg Arg Met Ile Gly Thr Asp Ala Phe Gln Glu
            195                 200                 205

Thr Pro Ile Val Glu Val Thr Arg Ser Ile Thr Lys His Asn Tyr Leu
210                 215                 220

Val Met Asp Val Glu Asp Ile Pro Arg Ile Ile Glu Glu Ala Phe Phe
225                 230                 235                 240

Leu Ala Thr Ser Gly Arg Pro Gly Pro Val Leu Val Asp Val Pro Lys
            245                 250                 255

Asp Ile Gln Gln Gln Leu Ala Ile Pro Asn Trp Glu Gln Ala Met Arg
        260                 265                 270

Leu Pro Gly Tyr Met Ser Arg Met Pro Lys Pro Pro Glu Asp Ser His
            275                 280                 285

Leu Glu Gln Ile Val Arg Leu Ile Ser Glu Ser Lys Lys Pro Val Leu
290                 295                 300

Tyr Val Gly Gly Gly Cys Leu Asn Ser Ser Asp Glu Leu Gly Arg Phe
305                 310                 315                 320

Val Glu Leu Thr Gly Ile Pro Val Ala Ser Thr Leu Met Gly Leu Gly
            325                 330                 335

Ser Tyr Pro Cys Asp Asp Glu Leu Ser Leu His Met Leu Gly Met His
            340                 345                 350

Gly Thr Val Tyr Ala Asn Tyr Ala Val Glu His Ser Asp Leu Leu Leu
            355                 360                 365

Ala Phe Gly Val Arg Phe Asp Asp Arg Val Thr Gly Lys Leu Glu Ala
370                 375                 380

Phe Ala Ser Arg Ala Lys Ile Val His Ile Asp Ile Asp Ser Ala Glu
385                 390                 395                 400

Ile Gly Lys Asn Lys Thr Pro His Val Ser Val Cys Gly Asp Val Lys
            405                 410                 415
```

Leu Ala Leu Gln Gly Met Asn Lys Val Glu Asn Arg Ala Glu Glu
            420                 425                 430

```
Arg Gln Gly Val Thr Asp Val Phe Ala Tyr Pro Gly Gly Ala Ser Met
            100                 105                 110

Glu Ile His Gln Ala Leu Thr Arg Ser Pro Ile Ile Arg Asn Val Leu
            115                 120                 125

Pro Arg His Glu Gln Gly Gly Val Phe Ala Ala Glu Gly Tyr Ala Arg
            130                 135                 140

Ala Ser Gly Lys Pro Gly Val Cys Ile Ala Thr Ser Gly Pro Gly Ala
145                 150                 155                 160

Thr Asn Leu Val Ser Gly Leu Ala Asp Ala Leu Leu Asp Ser Val Pro
                    165                 170                 175

Ile Val Ala Ile Thr Gly Gln Val Pro Arg Arg Met Ile Gly Thr Asp
                180                 185                 190

Ala Phe Gln Glu Thr Pro Ile Val Glu Val Thr Arg Ser Ile Thr Lys
                195                 200                 205

His Asn Tyr Leu Val Leu Asp Val Asp Asp Ile Pro Arg Ile Val Ser
            210                 215                 220

Glu Ala Phe Phe Leu Ala Thr Ser Gly Arg Pro Gly Pro Val Leu Ile
225                 230                 235                 240

Asp Val Pro Lys Asp Ile Gln Gln Gln Leu Ala Val Pro Asn Trp Asn
                245                 250                 255

Thr Pro Ile Lys Leu Pro Gly Tyr Met Ser Arg Leu Pro Lys Val Pro
                260                 265                 270

Asn Glu Ser His Leu Glu Gln Ile Val Arg Leu Ile Phe Glu Ser Lys
            275                 280                 285

Lys Pro Val Leu Tyr Val Gly Gly Gly Cys Leu Asn Ser Ser Glu Glu
290                 295                 300

Leu Arg Lys Phe Val Glu Leu Thr Gly Ile Pro Val Ala Ser Thr Leu
305                 310                 315                 320

Met Gly Leu Gly Ala Phe Pro Val Gly His Glu Leu Ser Leu Gln Met
                325                 330                 335

Leu Gly Met His Gly Thr Val Tyr Ala Asn Tyr Ser Val Asp Lys Ser
                340                 345                 350

Asp Leu Leu Leu Ala Phe Gly Val Arg Phe Asp Ala Arg Val Thr Gly
                355                 360                 365

Lys Leu Glu Ala Phe Ala Ser Arg Ala Lys Ile Val His Ile Asp Ile
370                 375                 380

Asp Ser Ala Glu Ile Gly Lys Asn Lys Gln Pro His Val Ser Val Cys
385                 390                 395                 400

Ala Asp Val Lys Phe Ala Leu Gln Gly Met Asn Lys Ile Leu Glu Ser
                405                 410                 415

Arg Cys Ala Lys Ser Lys Leu Asp Phe Lys Ala Trp Arg Glu Glu Leu
                420                 425                 430

Asn Glu Gln Lys Ser Lys Tyr Pro Leu Lys Tyr Lys Thr Phe Gly Asp
            435                 440                 445

Ala Ile Pro Pro Gln Tyr Ala Ile Gln Val Leu Asp Glu Leu Thr Asp
450                 455                 460

Gly Asn Ala Ile Ile Ser Thr Gly Val Gly Gln His Gln Met Trp Ala
465                 470                 475                 480

Ala Gln Phe Tyr Lys Tyr Lys Arg Pro Arg Gln Trp Leu Thr Ser Gly
                485                 490                 495

Gly Leu Gly Ala Met Gly Phe Gly Leu Pro Ala Ala Ile Gly Ala Ala
                500                 505                 510
```

```
Val Ala Asn Pro Gly Ala Val Val Asp Ile Asp Gly Asp Gly Ser
            515                 520                 525

Phe Ile Met Asn Val Gln Glu Leu Ala Thr Ile Arg Val Glu Asn Leu
    530                 535                 540

Pro Ile Lys Ile Met Leu Leu Asn Asn Gln His Leu Gly Met Val Val
545                 550                 555                 560

Gln Ser Glu Asp Arg Phe Tyr Lys Ala Asn Arg Ala His Thr Tyr Leu
                565                 570                 575

Gly Asp Pro Ser Lys Glu Ser Glu Ile Phe Pro Asn Met Leu Lys Phe
            580                 585                 590

Ala Glu Ala Cys Gly Ile Pro Ala Ala Arg Val Thr Arg Lys Glu Gly
        595                 600                 605

Leu Arg Met Ala Ile Gln Lys Met Leu Asp Thr Pro Gly Pro Tyr Leu
    610                 615                 620

Leu Asp Val Ile Val Pro His Gln Glu His Val Leu Pro Met Ile Pro
625                 630                 635                 640

Ser Gly Gly Ala Phe Lys Asp Val Ile Thr Glu Gly Asp Gly Arg Thr
                645                 650                 655

Lys Tyr

<210> SEQ ID NO 6
<211> LENGTH: 23
<212> TYPE: DNA
<213> ORGANISM: Artificial Sequence
<220> FEATURE:
<223> OTHER INFORMATION: Synthetic: crRNA region spacer sequence

<400> SEQUENCE: 6
acgaggaggg gcttgggttg tgg                                              23

<210> SEQ ID NO 7
<211> LENGTH: 27
<212> TYPE: DNA
<213> ORGANISM: Artificial Sequence
<220> FEATURE:
<223> OTHER INFORMATION: Synthetic: AHAS1 sgRNA

<400> SEQUENCE: 7
atttgggaat ggtggtacaa tgggagg                                          27

<210> SEQ ID NO 8
<211> LENGTH: 34
<212> TYPE: DNA
<213> ORGANISM: Artificial Sequence
<220> FEATURE:
<223> OTHER INFORMATION: Synthetic: AHAS2 sgRNA

<400> SEQUENCE: 8
gaacaatcaa catctgggta tggttgttca atgg                                  34

<210> SEQ ID NO 9
<211> LENGTH: 113
<212> TYPE: DNA
<213> ORGANISM: Artificial Sequence
<220> FEATURE:
<223> OTHER INFORMATION: Synthetic: AHAS1-2-C GRON

<400> SEQUENCE: 9
tctgccaatt aaaataatgc ttttgaataa tcagcatttg ggaatggtgg tacaatcgga      60
agaccgattc tacaaggcta atagagctca tacttatttg ggggatccat caa            113
```

```
<210> SEQ ID NO 10
<211> LENGTH: 113
<212> TYPE: DNA
<213> ORGANISM: Artificial Sequence
<220> FEATURE:
<223> OTHER INFORMATION: Synthetic: AHAS2-2-C GRON

<400> SEQUENCE: 10
acctgcctgt gaagatcttg ttactgaaca atcaacatct gggtatggtt gttcagtcgg        60
aggacagatt ctatcattcc aacagagcac atacatattt agggaaccca tca             113
```